(12) United States Patent
Emery

(10) Patent No.: US 6,838,446 B1
(45) Date of Patent: Jan. 4, 2005

(54) VECTOR FOR EXPRESSION OF GPI-ENZYME HYBRID

(75) Inventor: Stephen C. Emery, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/959,007

(22) PCT Filed: Apr. 28, 2000

(86) PCT No.: PCT/GB00/01640

§ 371 (c)(1),
(2), (4) Date: Oct. 17, 2001

(87) PCT Pub. No.: WO00/66752

PCT Pub. Date: Nov. 9, 2000

(30) Foreign Application Priority Data

May 1, 1999  (GB) .............................................. 9910077

(51) Int. Cl.$^7$ ........................ A61K 48/00; C12N 15/52; C12N 15/85

(52) U.S. Cl. ...................... 514/44; 435/320.1; 435/455; 424/93.2

(58) Field of Search ...................... 424/93.2; 435/320.1, 435/455; 514/44

(56) References Cited

U.S. PATENT DOCUMENTS

| | | | |
|---|---|---|---|
| 5,109,113 A | 4/1992 | Caras et al. | ................. 530/350 |
| 5,264,357 A | 11/1993 | Caras et al. | ............ 435/252.33 |
| 5,374,548 A | 12/1994 | Caras | ......................... 424/450 |
| 5,418,147 A | 5/1995 | Huang et al. | ............... 435/69.1 |

FOREIGN PATENT DOCUMENTS

| | | |
|---|---|---|
| EP | 0244267 B1 | 11/1987 |
| WO | WO 89/01041 | 2/1989 |
| WO | WO 94/01463 | 1/1994 |
| WO | WO 96/03515 A2 | 2/1996 |
| WO | WO 97/19180 | 5/1997 |
| WO | WO 98/51787 | 11/1998 |

OTHER PUBLICATIONS

Ali et al., "A protein targeting signal that functions in polarized epithelial cells in vivo", Biochem., 1996, vol. 315, pp. 857–862.

Anthony et al., "The Biological Chemistry of Folate Receptors", Blood, The Journal of The American Society of Hematology, Jun., 1992, pp. 2807–2820.

Clissold, "A cDNA construct of tissue inhibitor of metalloproteinases (TIMP) linked to the last exon of Thy–1 confers glycophospholipid anchorage on this naturally secreted protein", Biochem. J., 1992, vol. 281, pp. 129–136.

Clissold et al., "Construction, expression and functional analysis of glycolipid–linked form of CRI", Eur J Immunol, vol. 23, 1993, pp. 2346–2352.

Clissold, "Recombinant glycosyl–phosphatidylinositol–anchored proteins are not associated with protein kinases in trasfected thymoma cells", Biochem. J., 1994, vol. 304, pp. 853–859.

Douglas et al., "Targeted gene delivery by tropism–modified adenoviral vectors", Nature Biotechnology, Nov. 1996, vol. 14, pp. 1574–1578.

Douglas et al., "Targeted Gene Therapy", Tumor Targeting, 1995, vol. 1, pp. 67–84.

Harrison et al., "A convenient method for the construction and expression of GPI–anchored proteins", Nucleic Acid Research, 1994, vol. 22, No. 18, pp. 3813–3814.

Hooper, "Glycosyl–phosphatidylinositol anchored membrane enzymes", Clinica Chimica Acta, 1997, vol. 266, pp. 3–12.

Hooper et al., "Identification of membrane dipeptidase as a major glycosyl–phosphatidylinositol–anchored protein of the pancreatic zymogen granule membrane, and evidence for its release by phospholipase A", Biochem. J. 1997, vol. 324, pp. 151–157.

Kennard et al., GPI–Anchored Fusion Proteins, Methods of Biotechnology, vol. 8, Animal Cell Biotechnology, 1999, pp. 187–199.

Kinoshita et al., "GPI–Anchor Synthesis in Mammalian Cells: Genes, Their Products, and a Deficiency", J. Biochem., 1997, vol. 122, pp. 251–257.

Lisanti et al., "Fusion proteins containing a minimal GPI–attachment signal are apically expressed in trasfected MDCK cells", Journal of Cell Science, 1991, vol. 99, pp. 637–640.

Lowenstein et al., "Simultaneous detection of amplicon and HSV–1 helper encoded proteins reveals that neurons and astrocytoma cells do express amplicon–borne transgenes in the absence of synthesis of virus immediate early proteins", Molecular Brain Research, 1995, vol. 30, pp. 169–175.

Moran et al., "Proteins Containing an Uncleaved Signal for Glycophosphatidylinositol Membrane Anchor Attachment are Retained in a Post–ER Compartment", Journal of Cell Biology, Nov. 1992, vol. 119, No. 4, pp. 763–772.

Robbins et al., "Viral Vectors for Gene Therapy", Pharmacol. Ther., 1998, vol. 80, No. 1, pp. 35–47.

Soole et al., "A glycosyl–phosphatidylinositol anchor can target a bacterial enzyme to the apical surface of polarized epithelial cells", Biochemical Society Transactions, 1992, p. 21.

ten Dam et al., "Cell surface GPI–anchoring of CD45 isoforms", Molecular Biology Reports, 1998, vol. 25, pp. 197–204.

Udenfriend et al., "How Glycosylphosphatidylinositol–Anchored Membrane Proteins are Made", Annu. Rev. Biochem, 1995, vol. 64, pp. 563–591.

(List continued on next page.)

*Primary Examiner*—Scott D. Priebe
(74) *Attorney, Agent, or Firm*—Morgan, Lewis & Bockius LLP

(57) ABSTRACT

This invention relates particularly to gene directed enzyme prodrug therapy (GDEPT) using post translational glycosylphosphatidylinositol (GPI addition to a prodrug activating enzyme to enable anchorage of the enzyme at the cell surface, particularly for use in cancer therapy. A preferred prodrug activating enzyme is carboxypeptidase G2.

6 Claims, 4 Drawing Sheets

OTHER PUBLICATIONS

Verkman et al., "Endosomes from kidney collecting tubule cells cotnain the vasopressin–sensitive water channel", Nature, May 1988, vol. 333, pp. 268–272.

Hamstra, D.A. et al.: "Expression of Endogenously Activated Secreted or Cell Surface Carboxypeptidase A Sensitizes Tumor Cells to Methotrexate–alpha–Peptide Prodrugs" Cancer Research, vol. 60, No. 3, Feb. 1, 2000, pp. 657–665, XP000926076 the whole document.

Seki, T. et al.: "The human Thy–1 gene: Structure and chromosomal location" Proceedings of the National Academy of Sciences of USA, vol. 82, No. 19 Oct. 1985, pp. 6657–6661, XP000926079, the whole document.

Marais, R. et al. : "A cell surface tethered enzyme improves efficiency in gene–directed enzyme prodrug therapy" Nature Biotechnology, vol. 15, No. 13, Dec. 1997, pp. 1373–1377, XP002079969 cited in the application, the whole document.

VECTOR FOR EXPRESSION OF GPI-ENZYME HYBRID

This application is the National Phase of International Application PCT/GB00/01640 filed Mar. 25, 2000 which designated the U.S. and that International Application was published under PCT Article 21(2) in English.

This invention relates particularly to gene directed enzyme prodrug therapy (GDEPT) using post translational glycosylphosphatidylinositol (GPI) addition to a prodrug activating enzyme to enable anchorage of the enzyme at the cell surface, particularly for use in cancer therapy. In another aspect, the invention relates to an expression vector for expression of a CPG2-polypeptide anchor hybrid for use as a medicament wherein the CPG2 comprises unaltered glycosylation sites.

GDEPT is the subject of International Patent Application WO 98/51787, Zeneca Limited, and the reader is directed thereto for both general background information and detailed information on general experimental methods and materials. Marais et al (1997) Nature Biotechnology 15, 1373, described a cell surface anchored enzyme, CPG2, for GDEPT (see also WO 96/03515, Cancer Research Technology Limited). The enzyme was anchored by a transmembrane region from c-erb B2 fused to the C-terminus of the CPG2 enzyme. In use, a gene encoding the enzyme is administered to a mammal, and after a suitable time delay, prodrug is administered. Prodrug is converted to drug by the enzyme and this leads to cell death of e.g. tumour cells. There is a need for alternative means of anchoring enzymes to the surface of cells, particularly for GDEPT. Furthermore, WO 96/03515 stated that use of CPG2 for GDEPT in a form which could be glycosylated would not work because glycosylated CPG2 was inactive. Thus there is a need to provide a means for use of glycosylatable CPG2 for GDEPT.

The present invention is based on the discovery that a prodrug activating enzyme can be anchored to a cell surface via post-translational addition of a GPI anchor.

According to one aspect of the present invention there is provided an expression vector for expression of a glycosylphosphatidylinositol(GPI)-enzyme hybrid capable of anchorage to a surface of a mammalian cell comprising:
 i) a polynucleotide sequence which encodes a signal peptide;
 ii) a polynucleotide sequence which encodes an enzyme capable of activating a prodrug;
 iii) a polynucleotide sequence which encodes a post-translational GPI addition motif; and
 wherein
 sequences i), ii) & iii) are functionally positioned in this order relative to each other in the 5' to 3' direction of the sense strand of the vector;
 the enzyme does not have a GPI addition where the enzyme occurs naturally;
 and whereby on expression of the vector in the mammalian cell, the enzyme is capable of anchorage to the surface of the cell via a GPI moiety post-translationally added to the enzyme by the mammalian cell whereby to form the GPI-enzyme hybrid.

Such a GPI-enzyme hybrid is secreted but retained at the cell surface by a C-terminal GPI membrane anchor, thus achieving display of active enzyme on the cell surface. The enzyme is available to convert a prodrug to its active drug form which can enter the enzyme displaying cell to effect its cell killing effect or alternatively diffuse to surrounding cells to exert a so-called "bystander" effect.

This approach may be used optionally in combination with any suitable specificity enhancing technique(s) such as targeted cell infection and/or tissue specific expression. The efficacy of GDEPT systems is linked to the successful expression of the transgene encoding the enzyme in its active form by the target cell and the availability of the prodrug for subsequent conversion to active drug. Without wishing to be bound by theoretical considerations, it is believed that GPI anchorage of enzyme may be advantageous over anchorage with a transmembrane domain through providing additional flexibility for the enzyme to attain optimum activity. Flexibility may be particularly important for enzymes like CPG2 which need to dimerise for optimum activity.

Background information on GPI anchorage and display of proteins at the cell surface is set out below. GPI anchorage utilises a glycolipid termed GPI which is post-translationally linked to the carboxy-terminus of a protein via an amide bond (Undenfriend, S et al, Annu. Rev. Biochem 64, 563–591, 1995). Further references include: Hooper (1997) Clinica Chimica Acta, 266, 3–12; Kinoshita (1997) J. Biochem 122, 251–257; Harrison (1994) Nucleic Acids Research 22, 3813–3814; Kennard et al in Methods in Biotechnology, Vol 8 Animal Cell Biotechnology, 187–199, edited by Jenkins, Humana Press Inc., Totowa, N.J.; and Gilliland (1999) J. Immunol. 162, 3663–3671. Such GPI anchors are ubiquitous in eukaryotes and are employed by a wide variety of cell surface glycoproteins e.g. the folate receptor (Antony, A. C., Blood, 79, 2807–2820, 1992). Furthermore, naturally secreted proteins can be engineered for post translational GPI anchorage by the addition of the last exon of the Thy1 (rat brain antigen glycophospolipid-linked protein). The utility of this strategy was proven in experiments to achieve surface display of TIMP on both transiently transfected COS and stably transfected BW 5147 thymoma cells (Clissold, M. Biochem. J., 281,129–136, 1992) and in neurones and astrocytes using herpesvirus vectors (Lowenstein et al, 1994, Neuroscience 60:1059–77).

"Capable of anchorage" refers to the ability of the GPI-enzyme hybrid to be anchored in a membrane at a cell surface via the GPI portion thereof whilst leaving the enzyme substantially active and positioned close to, but not in, the cell membrane.

"Expression vector" refers to nucleic acid vector constructs to direct the transcription of nucleic acid in host cells. Expression vectors include but are not limited to plasmids, retroviral vectors, viral and synthetic vectors.

"GPI-enzyme hybrid" refers to the fusion between the enzyme and a GPI moiety post-translationally added to the enzyme by a mammalian cell on expression of a vector of the invention in the mammalian cell.

"Post-translational GPI addition motif" refers to that portion of a protein which confers the property of GPI anchorage thereon. For example, for Thy-1 it is encoded by last exon thereof. Other known motifs are described in Kennard et al in Methods in Biotechnology, Vol 8 Animal Cell Biotechnology, 187–199, edited by Jenkins, Humana Press Inc., Totowa, N.J.; see particularly Table 1 and, sections 1.1 and 1.2 therein, which describe the general features of such motifs (called "PAS" or pre-anchor sequence therein) including synthetic motifs. In general the following parts have been noted: a tripeptide which is a cleavage/attachment domain; a spacer domain; and a hydrophobic domain.

Thus the nascent form of a GPI anchored protein contains a hydrophobic cleavable N-terminal signal sequence that directs it to the endoplasmic reticulum for processing and a second hydrophobic peptide of 17–30 ammo acids at the C-terminus to direct GPI anchor addition to the protein. The cleavage and GPI anchor attachment site is N-terminal to the second hydrophobic peptide but separated by a hydrophilic spacer of between 5–10 amino acids. (Hooper N. M. Clinica Chimica Acta 266: 3–12). The GPI anchor is preformed within the endoplasmic reticulum possessing a common core structure and is attached to the carboxy terminus of the protein when a COOH group is exposed following the hydrophobic peptide cleavage. The conserved core structure is generally ethanolamine-$PO_4$-(mannose)$_3$-glucosamine-inositol-$PO_4$-lipid. Attached to the core structure may be a variety of side chain modifications which can be protein or tissue type specific and to date all GPI anchored proteins exhibit an additional ethanolamine phosphate on the 2-position of the mannose linked next to glucosamine (Kinoshita T. 1997 J. Biochem. 122:251–257).

Preferred motifs include decay accelerating factor (DAF); human placental alkaline phosphatase (HPAP), lymphocyte function associated antigen-3 (LFA-3) and Thy-1 C-terminal sequences with the latter being especially preferred. DAF has also been described in U.S. Pat. No. 5,109,113 & U.S. Pat. No. 5,264,357 (Caras etal).

"Functionally positioned" refers to ordering of the vector components so that they work together to achieve expression of polynucleotide that encodes protein in a form for post translational GPI addition.

An "enzyme capable of activating a prodrug" is defined as an enzyme for turning over a prodrug that has been administered to a host in which the enzyme is not naturally present in the relevant compartment of the host. Preferred enzymes are those suitable for use in ADEPT (for an explanation of ADEPT see below). For example, the enzyme may be foreign to the mammalian host (e.g. a bacterial enzyme like CPG2) or it may not naturally occur within the relevant host compartment (e.g. the use of lysozyme as an ADEPT enzyme is possible because lysozyme does not occur naturally in the circulation, see U.S. Pat. No. 5,433,955, Akzo NV). The relevant host compartment is that part of the mammalian host in which the substrate is distributed. Preferred enzymes are enzymes suitable for ADEPT or AMIRACS; see Bagshawe (1994) in Cell Biophysics 24/25, 83–91) but ADEPT enzymes are preferred. ADEPT is a known cancer therapeutic approach. ADEPT uses a tumour selective antibody conjugated to an enzyme. The conjugate is administered to the patient (usually intravenously), allowed to localise at the tumour site(s) and clear from the blood and other normal tissues. A prodrug is then administered to the patient which is converted by the enzyme (localised at the tumour site) into a cytotoxic drug which kills the tumour cells.

In International Patent Application WO 96/20011, published 4, Jul. 1996, we proposed a "reversed polarity" ADEPT system based on mutant human enzymes having the advantage of low immunogenicity compared with for example bacterial enzymes. A particular host enzyme was human pancreatic CPB (see for example, Example 15 [D253K]human CPB & 16 [D253R]human CPB therein) and prodrugs therefor (see Examples 18 & 19 therein). The host enzyme is mutated to give a change in mode of interaction between enzyme and prodrug in terms of recognition of substrate compared with the native host enzyme. In our subsequent International Patent Application No PCT/GB96/01975 (published 6, Mar. 1997 as WO 97/07796) further work on mutant CPB enzyme/prodrug combinations for ADEPT are described.

Preferred enzymes suitable for ADEPT are any one of CPG2 or a reversed polarity CPB enzyme, for example any one of [D253K]HCPB, [G25 ITD253K]HCPB or [A248S, G251T,[D253K]HCPB. In one embodiment, a preferred form of CPG2 is one in which the polypeptide glycosylation sites have been mutated so as to prevent or reduce glycosylation on expression in mammalian cells (see WO 96/03515, Cancer Research Campaign Technology); this may give improved enzyme activity.

In another embodiment of the invention, a preferred form of CPG2 comprises unaltered glycosylation sites. Use of CPG2 in this form has been surprisingly demonstrated, over the teaching in WO 96/03515 (Cancer Research Campaign Technology; see page 39, lines 18–20), to retain substantial activity even when glycosylated (see Example 1g below).

Further considerations arise for enzymes such as CPB which require a pro domain to facilitate correct folding; here the pro domain can either be expressed separately (in trans) or expressed as part of the fusion protein and subsequently removed.

Large scale purification of CPG2 from Pseudomonas RS-16 was described in Sherwood et al (1985), Eur, J. Biochem., 148, 447–453. CPG2 may be obtained from Centre for Applied Microbiology and Research, Porton Down, Salisbury, Wiltshire SP40 JG, United Kingdom. CPG2 may also be obtained by recombinant techniques. The nucleotide coding sequence for CPG2 has been published by Minton, N. P. et al., Gene, 31 (1984), 31–38. Expression of the coding sequence has been reported in *E.coli* (Chambers, S. P. et al., Appi. Microbiol, Biotechnol. (1988), 29, 572–578) and in *Saccharomyces cerevisiae* (Clarke, L. E. et al., J. Gen Microbiol, (1985) 131, 897–904). Total gene synthesis has been described by M. Edwards in Am. Biotech. Lab (1987), 5, 38–44. Expression of heterologous proteins in *E.coli* has been reviewed by F. A. O. Marston in DNA Cloning Vol. III, Practical Approach Series, IRL Press (Editor D M Glover), 1987, 59–88. Expression of proteins in yeast has been reviewed in Methods in Enzymology Volume 194, Academnic Press 1991, Edited by C. Guthrie and G R Fink.

A more preferred vector of the invention is one in which the prodrug activating enzyme is a bacterial enzyme optionally modified to alter one or more potential glycosylation sites recognisable by a mammalian cell so as to reduce glycosylation when expressed therein. A more preferred vector of the invention is one in which the prodrug activating enzyme is a carboxypeptidase. An especially preferred vector of the invention is one in which the prodrug activating enzyme is carboxypeptidase G2.

Examples of ADEPT systems include those based on any of the following enzymes: carboxypeptidase G2; carboxypeptidase A; aminopeptidase; alkaline phosphatase; glycosidases; β-glucuronidase; penicillin amidase; β-lactamase; cytosine deaminase; nitroreductase; or mutant host enzymes including carboxypeptidase A, carboxypeptidase B, and ribonuclease. Suitable references on ADEPT systems include Melton R G (1996) in J. S National Cancer Institute 88, 1; Niculescu-Duvaz I(1995) in Current Medicinal Chemistry 2, 687; Knox R J (1995) in Clin. Immunother. 3, 136; WO 88/07378 (CRCT); Blakey et al, Cancer Res. 56, 3287–92, 1996; U.S. Pat. No. 5,587,161 (CRCT and Zeneca); WO 97/07769 (Zeneca); and WO 95/13095 (Wellcome). The enzyme may be in the form of a catalytic antibody; see for example EP 745673 (Zeneca). Review articles on ADEPT systems include Hay & Denny (1996), Drugs of the Future, 21(9), 917–931 and Blakey (1997), Exp. Opin. Ther. Patents, 7(9), 965–977.

Whilst cancer therapeutic approaches are preferred, the invention may also be applied to other therapeutic areas as long as a target can be selected and a suitable enzyme/ prodrug combination prepared. For example, inflammatory diseases such as rheumatoid arthritis may be treated by for example using an enzyme capable of converting an anti-inflammatory drug in the form of a prodrug into an anti-inflammatory drug.

In another embodiment of the invention a preferred carboxypeptidase is selected from [D253K]HCPB, [G251T, D253K]HCPB or [A248S,G251T,D253K]HCPB.

It is contemplated that should it be possible to obtain a natural multimeric enzyme in monomeric form whilst substantially retaning enzymic activity, then the monomeric form of the enzyme could be used in the invention.

A preferred vector according to the invention is one in which the post-translational GPI addition motif is the last exon of Thy-1. Other suitable motifs include the C-terminal 31 amino acids of LFA-3 (Harrison et al, 1994, NAR, 22: 3813–3814).

An especially preferred vector according to the invention comprises:
  i) the post-translational lipid addition motif encodes SEQ ID NO: 12; and
  ii) the enzyme is carboxypeptidase G2.

The last exon of Thy 1 encodes 37 amino acids of the Thy 1 protein. This is post-translationally processed in the endoplasmic reticulum of the cell to remove 31 of the C-terminal amino acids and results in an amide bonded glycosylphosphatidyl inositol (GPI) moiety. This GPI enzyme hybrid (which contains a residual 6 amino acids of the Thy 1 protein) is then transported to the cell membrane and retained at the cell surface via GPI anchorage therein.

According to another aspect of the present invention there is provided a vector of the invention for use as a medicament.

According to another aspect of the invention there is provided a vector of the invention for manufacture of a medicamnent for cancer therapy in a mammalian host.

The invention is also based on the discovery that CPG2 comprising unaltered glycosylation sites can be expressed in mammalian cells in a glycosylated form which retains significant enzyme activity. Use of CPG2 in this form has been surprisingly demonstrated, over the teaching in WO 96/03515 (Cancer Research Campaign Technology; see page 39, lines 18–20), to retain substantial activity even when glycosylated (see Example 1g below).

Thus according to another aspect of the invention there is provided an expression vector for expression of a CPG2-polypeptide anchor hybrid for use as a medicament wherein the CPG2 comprises unaltered glycosylation sites.

Suitable polypeptide anchors and general experimental details are described in WO 96/03515 and Marais et al (1997) Nature biotechnology 15:1373. For example, a polypeptide anchor may be a transmembrane region, preferably from a transmembrane receptor kinase, especially c-erb b2, EGF receptor or CSF-1 receptor. Note that in this aspect of the invention, the expressed CPG2-polypeptide anchor hybrid requires no post-translational modification for cell membrane anchorage.

According to another aspect of the invention there is provided a two-component pharmaceutical composition comprising:
  a) a first component comprising an expression vector for expression of a CPG2-polypeptide anchor hybrid wherein the CPG2 comprises unaltered glycosylation sites and a pharmaceutically acceptable diluent or carrier, and
  b) a second component comprising a prodrug capable of activation by CPG2 and a pharmaceutically acceptable diluent or carrier.

The vector of the invention may be selectively expressed in target cells to restrict cell expression. Alternatively, the use of targeted vector delivery could be used to address the problem of specific tissue transfection and transgene expression. Methodologies in this area are discussed in reviews such as Douglas, J. T. and Curiel, D. T. Tumor targeting 1, 67–84, 1995, Douglas, J. T., et al, Nature Biotech. 14, 1574–1578, 1996 and Robbins, P. D., Pharmacol. Ther., 80, p35–47, 1998.

Any suitable delivery system may be applied to deliver the vector of the present invention including viral and non-viral systems and virus-like particles (VLPs). Viral systems include retroviral vectors, adenoviral vectors, adeno-associated virus, vaccinia, herpes simplex virus, HIV and other lentiviral vectors, the minute virus of mice, hepatitis B virus and influenza virus. Non-viral systems include uncomplexed DNA, DNA-liposome complexes, DNA-protein complexes and DNA-coated gold particles. A suitable VLP is for example polyoma.

Adenoviral vectors possess advantageous properties. They are capable of transducing a broad spectrum of human tissues and high levels of gene expression can be obtained in dividing and nondividing cells. Several routes of administration can be used including intravenous, intrabiliary, intraperitoneal, intravesicular, intracranial and intrathecal injection, and direct injection of the target organ. Thus targeting based on anatomical boundaries is feasible.

The adenoviral genome encodes 9 complex transciption units and infection involves a fiber protein to bind a cell surface receptor. The penton base of the capsid engages integrin receptor domainas ($\alpha_3\beta_3$, or $\alpha_3\beta_5$) on the cell surface resulting in internalization of the virus. Viral DNA enters the nucleus and begins transcription without cell division. Expression and replication is under control of the E1A region (see Horwitz, M. S., In Virology, $2^{nd}$ed., 1990, pp. 1723–1740). Removal of E1A renders the virus replicatior-incompetent. The use of attenuated bacteria, such as for example *Salmonella typhimurium*, which specifically target and replicate in hypoxic environments (such as are found in the necrotic centres of tumors) as gene delivery vehicles for prodrug enzyme based therapy (Tumour Amplified Prodrug Enzyme Therapy known as TAPET™) has also been proposed and is under development by Vion Pharmaceuticals. This system offers a further gene delivery alternative to the viral and non-viral delivery approaches discussed herein.

Nonviral DNA delivery strategies are also applicable. These DNA delivery systems include uncomplexed plasmid DNA, DNA-liposome complexes, DNA-protein complexes, and DNA-coated gold particles.

To improve the specificity of gene delivery and expression of the therapeutic gene, the inclusion of targeting elements into the delivery vehicles and the use of regulatory expression elements is contemplated.

The expression of a vector of the invention at its target site is preferably under the control of a transcriptional regulatory sequence CTR). A TRS is a promoter optionally combined with an enhancer and/or an control element such as a genetic switch described below.

One example of a TRS is a "genetic switch" that may be employed to control expression of a vector of the invention once it has been delivered to a target cell. Control of gene expression in higher eucaryotic cells by procaryotic regulatory elements (which are preferred for the present invention) has been reviewed by Gossen et al in TIBS, $18^{th}$ Dec. 1993, 471–475. Suitable systems include the *E.coli* lac operon and the especially preferred *E.coli* tetracycline resistance operon. References on the tetracycline system include Gossen et al (1995) Science 268, 1766; Damke et al (1995) Methods in Enzymology 257, Academic Press; Yin et al (1996) Anal. Biochem. 253, 195 and; patents U.S. Pat. No. 5,464,758, U.S. Pat. No. 5,589,362, WO 96/01313 and WO 94/29442 (Bujard). An ecdysone based switch (International Patent Appln No. PCT/GB96/01195, Publication No. WO 96/37609, Zeneca) is another option. Other options are listed below. Connaught Laboratories (WO-93/20218) describe a synthetic inducible eukaryotic promoter comprising at least two different classes of inducible elements. Rhone-Poulenc Rorer (WO 96/30512) describe a tetracycline-related application for a conditional gene expression system. Ariad (WO 94/18317) describes a protein dimerisation based system for which in vivo activity has been shown. Bert O'Malley of the Baylor College of Medicine (WO 93/23431, U.S. Pat. No. 5,364,791, WO 97/10337) describes a molecular switch based on the use of a modified steroid receptor. The Whitehead Institute have an NF-KB inducible gene expression system (WO 88/05083). Batelle Memorial have described a stress inducible promoter (European patent EP 263908).

Examples of TRSs which are independent of cell type include the following: cytomegalovirus promoter/enhancer, SV40 promoter/enhancer and retroviral long terminal repeat promoter/enhancer. Examples of TRSs which are dependent on cell type (to give an additional degree of targeting) include the following promoters: carcinoembryonic antigen (CEA) for targeting colorectal, lung and breast; alpha-foetoprotein (AFP) for targeting transformed hepatocytes; tyrosine hydroxylase, choline acetyl transferase or neurone specific enolase for targeting neuroblastomas; insulin for targeting pancreas and; glial fibro acidic protein for targeting glioblastomas. Some oncogenes may also be used which are selectively expressed in some tumours e.g. HER-2/neu or c-erbB2 in breast and N-myc in neuroblastoma.

Accordingly, a preferred vector for use as a medicament is a construct comprising a transcriptional regulatory sequence which comprises a promoter and a control element which is a genetic switch to control expression of the vector. A preferred genetic switch control element is regulated by presence of tetracycline or ecdysone. A preferred promoter is dependent on cell type and is selected from the following promoters: carcinoembryonic antigen (CEA); alpha-foetoprotein (AFP); tyrosine hydroxylase; choline acetyl transferase; neurone specific enolase; insulin; glial fibro acidic protein; HER-2/neu; c-erbB2; and N-myc. Preferably the vector for use as a medicament described herein is packaged within an adenovirus for delivery to the mammalian host. A general review of targeted gene therapy is given in Douglas et al., Tumor Targeting, 1995, 1 : 67–84.

The present invention can be applied to other GDEPT systems especially where naturally secreted enzymes are used. Suitable examples of GDEPT systems include those based on any of the following enzymes: carboxypeptidase G2; carboxypeptidase A; aminopeptidase; alkaline phosphatase; glycosidases; β-glucuronidase; penicillin amidase; β-lactamase; cytosine deaminase; nitroreductase; or mutant host enzymes including carboxypeptidase A, carboxypeptidase B, and ribonuclease. Suitable references on GDEPT systems include Mullen, C A., Pharmac. Ther. 63, 199–207, 1994; Connors, T. A., Gene Therapy, 2, 702–709, 1995; McNeish, I. A, et al, Advanced Drug Delivery Reviews, 26, 173–184 1997.

According to another aspect of the invention there is provided a pharmaceutical composition comprising a vector of the invention and a pharmaceutically acceptable diluent or carrier.

According to another aspect of the invention there is provided a pharmaceutical pack which comprises a first pharmaceutical composition of the invention as defined herein and a second pharmaceutical composition comprising a prodrug capable of activation by the enzyme in the first pharmaceutical composition and a pharmaceutically acceptable diluent or carrier. A preferred pharmaceutical pack comprises carboxypeptidase G2 enzyme and a nitrogen mustard prodrug.

According to another aspect of the present invention there is provided a matched two component system designed for use in a mammalian host in which the components comprise:

(i) a first component that comprises a vector of the invention and;

(ii) a second component that comprises a prodrug which can be converted into an active drug by enzyme which is encoded by the vector.

A preferred enzyme/prodrug combination is one in which: the enzyme is CPG2; and the prodrug is selected from N-(4-[N,N-bis(2-iodoethyl)amino]phenoxycarbonyl)-L-glutamic acid, N-(4-[N,N-bis(2-chloroethyl)amino]-phenoxycarbonyl)-L-glutamic-gamma-(3,5-dicarboxy) anilide or N-(4-N,N-bis(2-choroethyl)amino]-phenoxycarbonyl)-L-glutamic acid or a pharmaceutically acceptable salt thereof. Preferred prodrugs for use with CPG2 are described in the following US patents from Zeneca Limited and Cancer Research Campaign Technology Limited: U.S. Pat. No. 5,714,148, U.S. Pat. Nos. 5,405,990, 5,587,161 & 5,660,829.

According to another aspect of the present invention there is provided a GPI-enzyme hybrid suitable for attachment to a cell surface which is obtainable by mammalian cell expression of a vector of the invention defined herein.

According to another aspect of the present invention there is provided a host cell comprising a vector of the invention defined herein.

In another aspect of the invention there is provided a method for the delivery of a cytotoxic drug to a site which comprises administering to a host a first component that comprises a vector as defined herein; followed by administration to the host of a second component that comprises a prodrug which can be converted into a cytotoxic drug by the enzyme encoded by the first component. A preferred method for delivery of a cytotoxic drug to a site is one in which the first component comprises a gene encoding the enzyme CPG2; and the second component prodrug is selected from N-(4-[N,N-bis(2-iodoethyl)amino]-phenoxycarbonyl)-L-glutamic acid, N-(4[N,N-bis(2-chloroethyl)amino]-phenoxycarbonyl)-L-glutamic-gamma-(3,5-dicarboxy) anilide or N-(4-[N,N-bis(2-chloroethyl)amino]-phenoxycarbonyl)-L-glutamic acid or a pharmaceutically acceptable salt thereof.

The nucleotide sequences of the present invention may also be engineered in order to alter a coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, etc.

Abbreviations used herein include:

| | |
|---|---|
| ADEPT | antibody directed enzyme prodrug therapy |
| AMIRACS | Antimetabolite with Inactivation of Rescue Agents at Cancer Sites |
| APS | ammonium persulfate |
| b.p. | base pair |
| BPB | bromophenol blue |
| CPB | carboxypeptidase B |
| CPG2 | carboxypeptidase G2 |
| CPG2(Q3) or Q3 variant | CPG2 mutated to reduce glycosylation on expression in eucaryotic cells, preferably through mutating asparagine at positions 222, 264 & 272 to glutamine |
| CRD | Cross Reacting Determinant: when GPI anchored proteins are cleaved from a cell membrane by the enzyme PI-PLC, the released protein retains a small part of the GPI anchor, termed the CRD |
| CsCl | Caesium Chloride |
| distilled water | distilled water |
| DMEM | Dulbecco's modified Eagle's medium |
| DOPE | dioleoyl phosphatidylethanolamine |
| DOTMA | N-[1-(2,3-dioleyloxy)propyl]-n,n,n-trimethylammonium chloride |
| EIA | enzyme immunoassay |
| ELISA | enzyme linked immunosorbent assay |
| FACS | fluorescence activated cell sorting |
| FAS | folinic acid supplemented |
| FCS | foetal calf serum |
| FITC | fluorescein isothiocyanate |
| G418 (sulphate) | GENETICIN ™, GibcoBRL Cat. No. 11811, an aminoglycoside antibiotic related to gentamicin used as a selecting agent in molecular genetic experiments; |
| GDEPT | gene directed enzyme prodrug therapy |
| GPI | glycosylphosphatidylinositol |
| HCPB | human carboxypeptidase B, preferably pancreatic |
| HPLC | high performance liquid chromatography |
| HRPO or HRP | horse radish peroxidase |
| ICC | immunocytochemistry |
| MDCK | Madin Darby Canine Kidney (ATCC CCL 34 F-13627) |
| MOI | multiplicity of infection |
| NCIMB | National Collections of Industrial and Marine Bacteria |
| NEAA | non-essential amino acids |
| PBS | phosphate buffered saline |
| PCR | polymerase chain reaction |
| pfu | plaque forming units |
| PI-PLC | phosphatidylinositol phospholipase C |
| RCA | replication competent adenovirus |
| SDS-PAGE | sodium dodecyl sulphate - polyacrylamide gel electrophoresis |
| SSC | salt sodium citrate |
| TAPET ™ | Tumour Amplified Prodrug Enzyme Therapy |
| TIMP | tissue inhibitor of metalloproteinases |
| TRS | transcriptional regulatory sequence |
| VDEPT | virus-directed enzyme prodrug therapy |
| VH | variable region of the heavy antibody chain |
| VK | variable region of the light antibody chain |
| ZD2767 prodrug | N-(4-[N,N-bis(2-iodoethyl)amino]-phenoxycarbonyl)-L-glutamic acid (see U.S. Pat. No. 5405990) |

In this specification conservative amino acid analogues of specific amino acid sequences are contemplated which retan the relevant biological properties of the component of the invention but differ in sequence by one or more conservative amino acid substitutions, deletions or additions. However the specifically listed amino acid sequences are preferred. Typical conservative amino acid substitutions are tabulated below.

| Original | Suitable Substitutions | Preferred Substitutions |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp; Phe; Thr; Ser | Phe |
| Val (V) | Ile; Leu; Met; Phe; | Leu |

Ala; Norleucine

Amino acid nomenclature is set out below.
Alanine, Ala, A; Arginine, Arg, R; Asparagine, Asn, N; Aspartic Acid, Asp, D; Cysteine, Cys, C; Glutamic Acid, Glu, E; Glutamine, Gln, Q; Glycine, Gly, G; Histidine, His, H; Isoleucine, Ile, I; Leucine, Leu, L; Lysine, Lys, K; Methionine, Met, M; Phenylalanine, Phe, F; Proline, Pro, P; Serine, Ser, S; Threonine, Thr, T; Tryptophan, Trp, W; Tyrosine, Tyr, Y; Valine, Val, V; Any Amino Acid, Xaa, X.

In this specification nucleic acid variations (deletions, substitutions and additions) of specific nucleic acid sequences are contemplated which retain which the ability to hybridise under stringent conditions to the specific sequence in question. Stringent conditions are defined as 6×SSC, 0.1% SDS at 60° for 5 minutes. However specifically listed nucleic acid sequences are preferred. It is contemplated that chemical analogues of natural nucleic acid structures such as "peptide nucleic acid" (PNA) may be an acceptable equivalent, particularly for purposes that do not require translation into protein (Wittung (1994) Nature 368, 561).

The invention will now be illustrated by reference to the following non-limiting Examples Temperatures are in degrees Celsius.

therefore is most likely unglycosylated CPG2 indicating that the glycosylation process within the COS 7 cells was not 100% efficient. The two larger bands probably represent glycosylated CPG2 forms. The largest band had an approximate size of 66 KDa and the middle band 55 KDa. Tunicamycin addition completely blocks glycosylation of CPG2, with western analysis showing the expression of the single 43 KDa band representing unglycosylated CPG2 protein. Supernatant analysed from CPG2(Q3) expression gives a single band of 43 KDa, the mobility of which is unaffected by tunicamycin, proving that the mutagenesis of the three asparagine residues to glutamine residues has resulted in the expression of an uniform Q3 variant of the CPG2 protein. Lane 1=bacterial CPG2, Lanes 2–3=CPG2 (Q3), Lanes 4–5=CPG2,+=Tunicamycin present,–=Tunicamycin absent.

Figure 3:
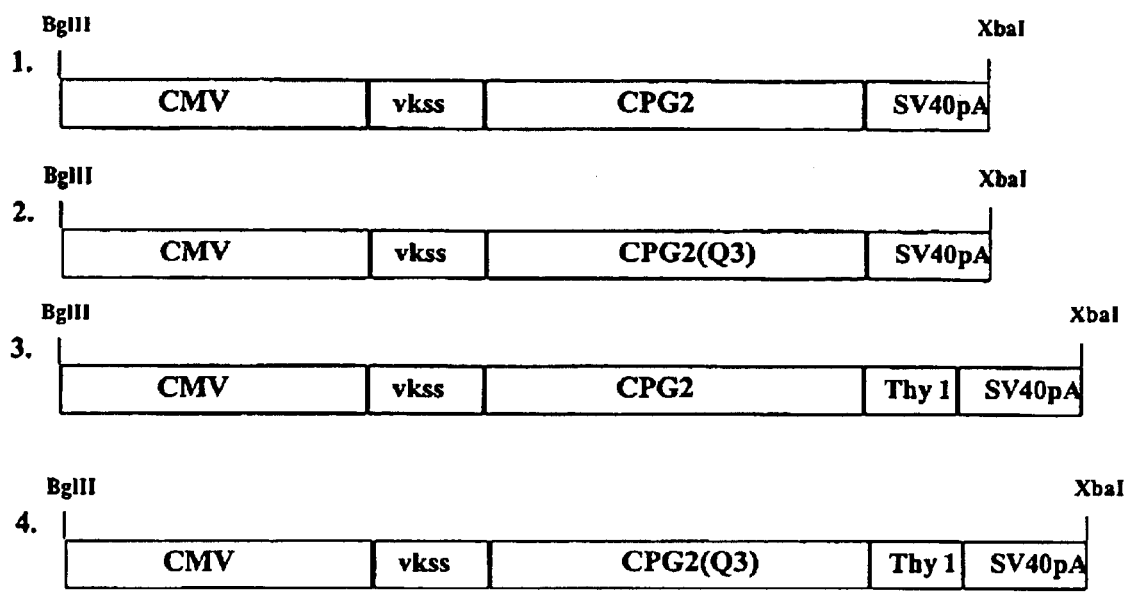

FIG. 3 illustrates the four CPG2 gene cassettes encoded within the replication defective Adenovirus (RAd) vectors. A table showing the sizes of the four CPG2 gene cassettes and the form of CPG2 protein encoded by each is set out below.

| Cassette No | Name | Size (bp) | CPG2 protein expression |
|---|---|---|---|
| 1 | CPG2 | 2312 | secreted, glycosylatable |
| 2 | CPG2(Q3) | 2312 | secreted, unglycosylated |
| 3 | CPG2-Thy 1 | 2414 | GPI anchored, glycosylatable |
| 4 | CPG2(Q3)-Thy 1 | 2414 | GPI anchored, unglycosylated |

Figure 4A:
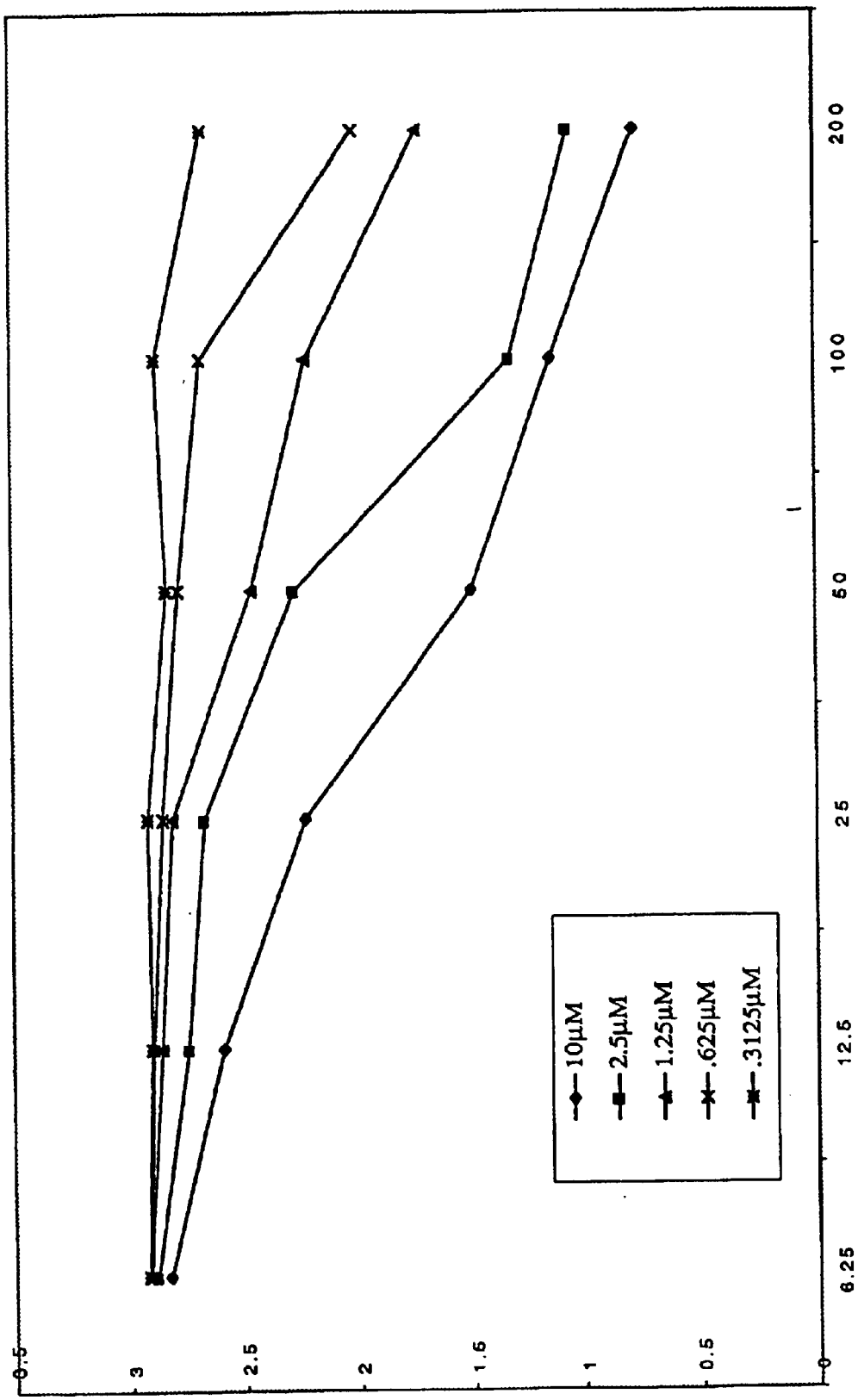
Figure 4:
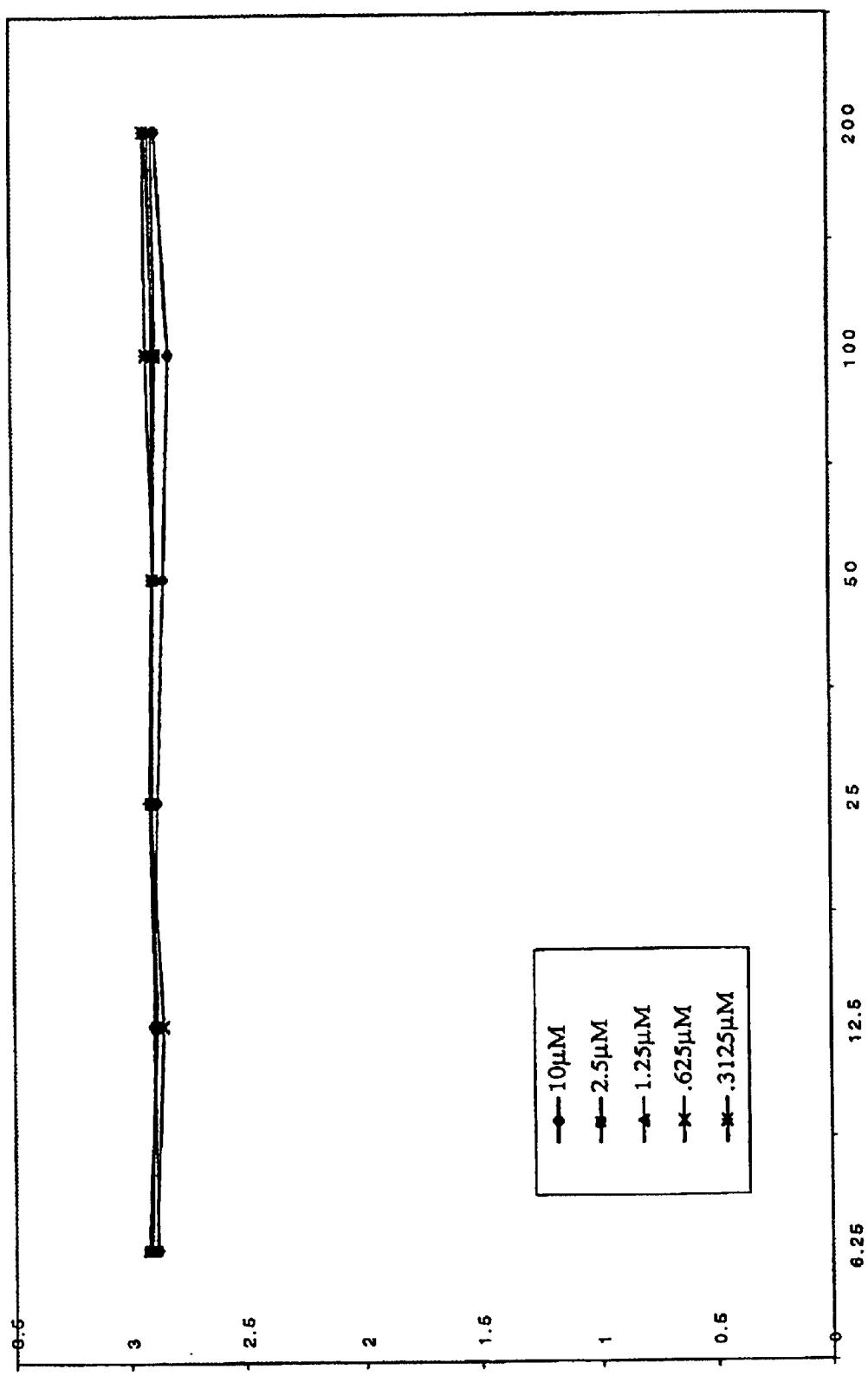

FIG. 4a demonstrates the in vitro cell killing capacity of RAd/CPG2(Q3)-Thy 1 adenovirus for Lovo tumour cells when varying the number of adenoviral pfu's (MOI) used for cell infection in combination with different concentrations of prodrug ZD2767P (see key). The vertical-axis denotes the OD 540 measurement following SRB staining and the horizontal-axis the adenoviral MOI used. A decrease in OD540 indicates a lower final number of Lovo cells and hence the achievement of a greater degree of cell killing. From the graph it can be observed that the level of cell killing improves with increasing prodrug concentration in a dose dependant manner with regard to the adenoviral MOI employed.

FIG. 4b, as described in FIG. 4a, this graph displays the in vitro cell killing capacity of RAd/CPG2(Q3) adenovirus for Lovo tumour cells. In this control experiment, the expressed CPG2 protein should not be retained at the cell surface and thus be removed on cell washing before addition of the prodrug (therefore there should be no enzymatic activity to convert the prodrug to active drug component). Unlike in FIG. 4a, it may be observed that at the prodrug concentrations used in this experiment there is little or no difference in the Lovo cell killing capacity irrespective of the dose of adenovirus given.

In the Examples below the following methodology and materials have been applied.

General molecular biology procedures can be followed from methods described in "Molecular Cloning—A laboratory manual" Second Edition, Sambrok, Fitsch and Maniatis (Cold Spring Harbour Laboratory, 1989).

Adenovirus construction, purification and infection procedures have been developed from Lowenstein, P. R and Enquist, L. W. (Eds) Protocols for Gene transfer in Neuroscience 1995 Wiley and Sons, New York.

A standard 50 μl Polymerase Chain Reaction contains 200 μM each of dNTP's (dATP, dCTP, dGTP, dTTP), 50 pM of each primer oligonucleotide and 1×PCR buffer (giving a final concentration of 50 mM KCl, 10 mM Tris/HCl pH 8.3, 1.5 mM $MgCl_2$ and 0.1% gelatin). After the addition of 100 mM of template DNA, the reaction is heated to 94° for 5 minutes using a thermal cycler, 2.5 units of the thermostable Taq polymerase (AMPLITAQ™ available from Perkin-Elmer Cetus) is added and the thermal cycling continued. Standard PCR conditions are 15 cycles with denaturation at 94° for 1 min, annealing at 55° for 1 min and extension at 72° for 1 min. A final extension at 72° for 10 minutes completes the cycling.

DNA recovery from agarose gels is accomplished by using a GENECLEAN™ II kit obtainable from Bio 101 Inc and developed from the method of Vogelstein and Gillespie., *Proceedings of the National Academy of Sciences USA* (1979) 76 p615. After weighing the gel embedded DNA 3 volumes of 6M NaI is added. The agarose is melted at 55° for 15 minutes and 10 ml of a specially formulated silica matrix in water, "Glassmilk" added, mixed and allowed to bind the DNA for 10 minutes on ice. The glassmilk/DNA complex is pelleted by centrifugation and washed 3 times with a NaCl/ethanol/water wash. The bound DNA is disassociated by dissolving in sterile water at 55° for 20 minutes.

Competent *E.coli* DH5α cells were obtained from Life Technologies Ltd (MAX™ efficiency DH5α competent cells) and transformed using a standard heat shock method.

Mini-preparations of double stranded plasmnid DNA were made using the RPM™ DNA preparation kit from Bio 101 Inc. (cat. No 2070-400) or a similar product—the kit contains alkaline lysis solution to liberate plasmid DNA from bacterial cells and glassmilk in a spinfilter to adsorb liberated DNA which is then eluted with sterile water or 10 mM Tris-HCl, 1 mM EDTA, pH 7.5.

Trypsinisation is used to detach adherent cell cultures. Trypsin EDTA (Gibco BRL 45300-019) and PBS is pre-warmed to 37°. Existing media is removed from the cultures and replaced with a volume of PBS to wash the cells. The PBS is removed and enough Trypsin solution added to just cover the cells. After 5 minutes the cells will detach and the trypsin is inactivated by the addition of the appropriate normal culture medium.

Heat inactivation of FCS is achieved by incubation at 56° for 15 minutes then stored at 20°.

Serum free medium is OPTIMEM™ I Reduced Serum Medium:, GibcoBRL Cat No. 31985. This is a miodification of Eagle's Minimum Essential Medium buffered with Hepes and sodium bicarbonate, supplemented with hypoxanthine, thymidine, sodium pyruvate, L-glutahne, trace elements and growth factors.

Transient tranfection of COS 7 cells can be achieved using a LIPOFECTIN™ based procedure. LIPOFECTIN™ Reagent (Gibco BRL Cat. No. 18292-011) is a 1:1 (w/w) liposome formulation of the cationic lipid DOTMA and DOPE in membrane filtered water. It binds spontaneously with DNA to form a lipid-DNA complex (Felgner et al., *Proc. Natl. Acad Sci. USA* (1987) 84, 7431. COS 7 cells are seeded into a 6 well plate a $2 \times 10^5$ cell/2 ml/well, from a subconfluent culture and incubated overnight at 37°, 5% $CO_2$. A LIPOFECTIN™/serum free medium mix is made up containing 120 μl LIPOFECTIN™ plus 480 μl serum free medium and incubated at room temperature for 30 minutes. A DNA/serum free medium mix is prepared by mixing 12 μg DNA with 600 μl serum free medium. The LIPOFECTIN™/serum free medium mix is added to the DNA/serum free medium mix and left at room temperature for 15 mins. The cells are washed once with 2 ml serum free-medium, then 800 μl serum free media added plus 200 μl LIPOFECTIN™/ DNA mix/well and incubated for 5 hours at 37°, 5% $CO_2$. The LIPOFECIN™/DNA mix is removed from the cells and normal growth media added after which the cells are incubated for 48–72 hours at 37°, 5% $CO_2$ when the supernatants are harvested.

COS 7 cells can also be transiently transfected in the presence of the glycosylation inhibitor tunicamycin. The transfection procedure is repeated as above, but after incubating for 5 hours at 37°, 5% $CO_2$, 10 μg/ml tunicamycin (Sigma T7765) is added into the normal growth media.

For the production of stable transfectants, in preparation for transfection, CHO K1 cell (ATCC CCL 61) were cultured in grow all media and passaged at least three times before transfection. For the transfection, a viable count (using a haemocytometer/trypan blue staining) of the adherent cells was made and the cells plated out at $2 \times 10^5$ cells per well into a 6 well plate (Costar 3516) and left for 18–24 hours for the cells to re-adhere.

For each individual transfection, 20 μl of LIPOFECIIN™ was added to 80 μl serum free medium and left at room temperature for 30 minutes. Plasmid DNA (2 μg) of interest was added to 100 μl serum free medium and subsequently added to the LIPOFECTIN™ mix and left for a further 15 minutes. The individual 6 well plates were washed with 2 ml serum free medium per well to remove any serum and replaced with 800 μl of fresh serum free medium. The 200 μl DNA/LIPOFECTIN™/serum free medium mixes which had been previously prepared were then added to each well of cells. The plates were incubated at 37° for 5 hours, the media removed and 2 ml of fresh normal media added and incubated for a further 48 hours. The transfected cells in the 6 well plate were scraped free, the cell suspension removed and centrifuged. All the supernatant was removed and the cell pellet resuspended in 20 ml of the appropriate fresh growth media containing the appropriate selective agent for the transfected DNA (e.g. G418). Aliquots (200 μl) were plated per well into a 96 well plate ($1.25 \times 10^4$ cells per well).

Colonies were allowed to develop for 10–14 days, then the supernatant screened by standard ELISA assay to detect CPG2 secretion or FACS analysis to detect membrane anchored CPG2 enzyme.

G418 Selection: for CHO K1 cells (ATCC CCL 61) selection was perfomned at 1.25 mg/ml.

Normal DMEM Media (using Gibco BRL components): To 500 ml DMEM (41966-086) add 12.5 ml Hepes (15630-056); 5 ml NEAA (11140-035); 5 ml pen/strep (10378-016); and 50 ml heat inactivated FCS.

Grow All Media (using Gibco BRL components): To 500 ml DMEM (41966-086) add 5 ml NEAA (1140-035); 5 ml pen/strep (10378-016); and 25 ml heat inactivated FCS and 50 ml horse serum.

FAS Media (using Gibco BRL components unless stated otherwise): 490 ml DMEM (41966-086); 12.5 ml Hepes (15630-056); 5 ml non-essential amino acids (11140-035); 5 ml pen/strep (10378-016); 5 ml vitamins (11120-037); 5 ml basal amino acids (51051-019); Folinic Acid (Sigma F8259) to a final media concentration of 10 μg/ml; 50 ml heat inactivated FCS; 5 ml dNTP mix; and G418 50 mg/ml stock solution (to produce the appropriate selection concentration).

dNTP mix: 35 mg G (Sigma G6264), 35 mg C (Sigma C4654). 35 mg A (Sigma A4036), 35 mg U (Sigma U3003), 125 mg T (Sigma T 1895) were dissolved in 100 ml water, filter sterilised, and stored at −20°.

For the CPG2 capture ELISA, 96 well plates precoated with goat anti-mouse IgG are used (PIERCE REACII-BIND™ 15134 plates). A second layer of mouse monoclonal anti-CPG2 diluted 1:800 in PBS/0.05% TWEEN™/BSA is added by overnight incubation at 4°. In between each binding step the plate is washed 3 times with PBS/0.05% TWEEN™. 100 μl test sample is added per well and doubling dilutions in PBS/0.05%TWEEN™ carried out across the plate. A fourth layer of rabbit polyclonal anti-CPG2 diluted 1:2500 in PBS/0.05% TWEEN™/2% BSA is added followed by a final layer of goat anit-rabbit IgG Horse Radish Peroxidase Labelled Antibody (DAKO PO448) diluted 1:1000 in PBS/0.05% TWEEN™/2% BSA. To detect binding, 100 μl per well of developing solution is added [one capsule of phosphate-citrate buffer (Sigma P4922) dissolved in 100 ml water to which is added one 30 mg tablet o-phenyldiamine dihydrochloride (Sigma P4812)] and the reaction stopped after 5 mins by adding 75 μl 2M $H_2SO_4$, and the absorbance read at 490 nm.

Western blot analysis of transfection supernatants to detect CPG2 was performed as follows Samples were prepared by denaturation in 1×Laemmli loading buffer (0.0675M Tris; 2% SDS; 15% glycerol; 2M urea; 0.001% BPB containing 2.5% β-mercaptoethanol.) 10% mini polyacrylamide gels are prepared using the mini gel system (HOEFER MIGHTY SMALL™). 10% running gel contains 20 ml acrylamide; 6 ml 10× running buffer, 34 ml water, 300 ml 20% SDS; 600 βl 10%APS; 30 μl TEMED. 10× running buffer contains 3.75M Tris pH 8.6. 6% stacking gel contains 9 mls acrylamide; 4.5 ml 10× stacking gel buffer 31.5 ml water, 225 ml 20% SDS; 450 μl 10% APS; 24 μl TEMED. 10× stacldng gel buffer is 1.25M Tris pH 6.8. 5× electrophorcsis buffer for SDS/PAGE is 249 mM Tris; 799 mM glycine; 0.6% w/v SDS (pH not adjusted). Samples are run alongside molecular weight markers (Amershamn RAN-BOW™ markers) and 10 ng/ml of CPG2 standard at 30 milliamps for approx 1 hour. The gel is blotted using a semi dry blotter (IKB) onto nitrocellulose membrane at 0.7× gel area ($cm^2$) milliamps for 45 mins. The membrane is blocked with 5% dried skimmed milk in PBS/0.05% TWEEN™ for 1 hour at room temperature.

For CPG2 detection: by overnight incubation at 4° with mouse monoclonal antiCPG2 (1/800 dilution in 0.5% dried skimmed milk in PBS/0.05% TWEEN™) followed by incubation for 2 h at room temperature with goat anti-mouse kappa light chain HRPO labelled antibody (Sigma 674301, diluted 1/10000 in 0.5% dried skimmed milk in PBS/0.05% Tween).

For CRD detection: by overnight incubation at 4° C. with rabbit anti-CRD (Oxford Glycosystems) (1/200 dilution in 0.5% dried skimmed milk in PBS/0.05% TWEEN™) followed by incubation for 2 h at room temperature with goat anti-rabbit IgG HRPO conjugated antibody (DAKO PO448) (diluted 1:1000 in 0.5% dried skimmed milk in PBS/10 0.05% TWEEN™).

The blot is developed using chemiluminescent detection of HRPO based on luminol substrate in the presence of enhancer (PIERCE SUPERSIGNAL SUBSTRATE™) 0.125 ml of luminol/enhancer and stable peroxide solution (1:1/v:v)/$cm^2$ of blot surface is incubated at room temperature on the blot for 5–10 mins then the blot is exposed against autoradiographic film for between 30 secs and 5 mins.

To measure CPG2 enzyme activity in cell supernatant samples at HPLC based CPG2 enzyme assay can be used. 125 βl cell supernatant is pulsed in a micro-centrifuge to remove cell debris and 375 μl fresh reaction buffer (PBS/0.2 mM $ZnCl_2$) added. Upon addition of 100 μM methotrexate, a substrate for the CPG2 enzyme, the reaction is incubated at 37° for 1 hour. The reaction is stopped by the addition of 500 µl methanol/0.2% Trifluoroacetio acid. The 1 ml sample is placed in a capped vial and assayed using HPLC. An isocratic separation with a mobile phase containing: 60% Methanol/40%, 60 mM Ammonium formate/0.1% Trifluoroacetic acid is used with an S5SCxcolumn (Hichrom). 60 µl of sample is injected and the absorbance at 300 nm measured over a total run time of 8 mins/sample giving expected retention times for methotrexate and metabolite of 3.9 and 5.6 respectively.

FACS is used to calculate the percentage of cells within a population that are expressing eithier intracellular CPG2 or extracellular CPG2 protein. Cells are harvested 48 hours after plasmid transient transfection or viral infection by trypsinisation. $10^6$ cell are aliquoted into FACS tubes and after washing with PBS they are resuspended in 4% paraformaldehyde fix (4% paraformaldehyde; 2% NaOH; 0.1M $NaH_2PO_4$. $2H_2O$; 0.12M sucrose) for 15 mins at 4°. To calculate intracellular CPG2 content the cells are permeabilised after a PBS wash to remove the fix by incubation in permeabilisadion buffer ((150 mM NaCl; 1 mM HEPES pH7.0; 4% foetal bovine serum; 0.1% TRITON™-X-100) on ice for 10 minutes. To analyse for extracellular CPG2 this step is omitted and the cells are only washed with PBS.

The cells are incubated with rabbit polyclonal-anti-CPG2 diluted 1:1000 in primary antibody solution (PBS; 200 µg/ml RNase A; 10 µg/ml propidium iodide; 10% BSA) for 2 hours at room temperature. After washing in PBS/1% BSA the cells are incubated with FITC-labelled goat anti-rabbit IgG (DAKO F0205) diluted 1:50 in staining buffer pH 7–8 (PBS; 1% heat inactivated FCS; 0.1% sodium azide) for 1 hour at ROOM TEMPERATURE in the dark. After washing PBS the cells are resuspended in PBS and analysed by FACS using ?

PI-PLC, for GPI anchor cleavage is isolated from *Bacillus thuringensis*, (Oxford Glycosystems). $10^6$ cells were treated with 1 unit/ml PI-Plc for 3 hours at 37° before FACS analysis upon unpermeabilised cells.

For ICC staining for CPG2 protein in adherent cell cultures, $10^4$ cells/well are seeded into 6 well plates into which sterile glass coverslips have been placed. The cells are transfected following the transient transfection method or infected with virus and expression allowed for 48 hours. After aspirating the media the cell covered coverslips are washed with PBS then fixed with 1 ml in 4% paraforialdehyde fix (4% paraformaldehyde; 2% NaOH; 0.1M $NaH_2PO_4.2H_2O$; 0.12M sucrose) for 20 minutes at room temperature. After each incubation step the cells are washed 3 times with PBS. To stain for intracellular CPG2 the cells are permeabilised by washing with PBS/0.1% TRITON-X-100 for 15 minutes at room temperature. Before antibody staining the cells are blocked with PBS/10% horse serum for 30 minutes at room temperature followed by incubation with PBS/1% horse serun. The cells are coated with the primary antibody rabbit polyclonal anti-CPG2 diluted 1:1000 in PBS/1% horse serum for 2 hours at room temperature in a plastic box containing damp paper towels in the dark The secondary antibody FITC-labelled goat-anti-rabbit IgG (DAKO F0205) diluted 1:50 in PBS/1% horse serum is used to coat the cells for a fuirther 2 hours at room temperature in a plastic box containing damp paper towels. After the PBS washes, the cell coated coverslips are coated with 1xDAPI solution (Sigma D9542) for 10 mins in the dark, then mounted onto glass slides using suitable mounting media (12% MOWIOL™; 34.5% glycerol; 0.12M Tris-HCl pH 8.5) ready for analysis.

Calcium pbosphate mediated DNA transfer is used to cotransfect shuttle plasmid and adenovirus genome plasmid into a 293 packaging cell line, allowing homologous recombination and production of a replication incompetent Adenovirus vector, (based on McGrory, W. J. et al., *Virology* (1988) 163, 614–617. 200 µl low TE buffer (1 mM Tris pH 7.5; 0.05 mM EDTA pH 8.0) is added to 5 µg shuttle plasmid DNA and 5 µg Adenovinis genome plasmid DNA in a 15 ml tube. After the addition of 30 µl 2M $CaCl_2$ the mixture is spun briefly. In a second 15 ml tube 240 µl 2xHBS buffer (0.28M NaCl; 0.05M Hepes; 0.001 5M $Na_2HPO_4$) is added, through which air is slowly bubbled using a Pasteur pipette. The contents of the first falcon tube are introduced dropwise into the 2xHBS at the same time and the mixture allowed to stand at room temperature for 30 minutes for a precipitate to form. A 25 $cm^2$ flask of 293 cells is grown to 40% confluency and after the addition of 7 ml of fresh 293 media the precipitate solution is added to the cells and left at 37°, 5% $CO_2$ for 16 hours. Thorough washing of the cells with PBS is used to remove precipitate, fresh 293 media, is added to the cells and is replaced every three days until viral cytopathic effect is observed in the form of plaques, usually visible 6–8 days after transfection. When cytopathic effect is observed throughout the flask the cells are easily detached by agitation of the flask and are harvested by centrifugation and resuspension in 300 µl 293 media.

Adenovirus DNA extraction from a 25 $cm^2$ flask of 293 cells following viral infection. The flask of 293 cells are cultured to 70% confluence then infected with 10 µl of viral stock produced from the co-transfection. As soon as the infected cells all become rounded they are spun down for 5 minutes at 300 g, rinsed in PBS and then spun again for 5 minutes at 300 g. The remainder of the procedure is carried out on ice. The cell pellet is re-suspended in 360 µl 1x Tris-EDTA pH 8; 25 µl 10% SDS; 8 µl 0.5M EDTA and 4 µl Proteinase K (20 mg/ml) before incubating at 37° for 2 hours. 100 µl of 5M NaCl is added and the tube kept on ice for at least 3 hours after which it was spun for 1 hour at 15000 g. Supernatant is then harvested, phenol:chloroform:isoamylalcohol (25:24:1) extracted and precipitated with 2 volumes of ethanol.

The DNA precipitate is then spun for 10 minutes at 15000 g, washed once with 70% ethanol and then re-suspended in 50 µl distilled water containing 0.1 mg/ml RNAse.

Adenovirus purification is achieved by end point dilution. 36 wells of a 96 well plate are plated with $8 \times 10^4$ 293 cells per well and incubated overnight at 37°, 5% $CO_2$. The media is replaced by triplicate serial dilutions of virus in 100 µl, ranging from $10^{-2}$ to $10^{-11}$. After 24 hours at 37°, 5% $CO_2$, 100 µl of fresh medium is added to each well and then at 3 day intervals the media replaced. The wells are monitored daily for plaque formation and after ~8 days of infection the last well with evidence of plaque formation identified. The cells in the end-point wells undergo 3 cycles of freeze thawing to crack open the cells and the cell debris is spun down. The whole process is repeated another 2 times using viral supernatant from the previous round of plaque purinfication. The final viral supernatant can be used for scaling up the vius.

To scale up virus stocks a 175 $cm^2$ flask of 70% confluent 293 cells is inoculated with 20 µl of end point virus from the third round of plaque purification. When 100% cytopathic effect is witnessed, cells are harvested and re-suspended in 500 µl PBS. The cells are cracked open by freeze thawing 3 times and the cell debris spun down. Supernatant is used to infect 15, 175 $cm^2$ flasks at a MOI of 3. When 100% cytopathic effect is observed the cells are ready for ARKLONE P™ purification. (ARKLONE P™, a chlorofluorocarbon that disrupts membrane lipids and thus lyses cells, was obtained from ICI Chlor-Chemicals.)

ARKLONE P™ purification of 293 cells from 15 175 cm² flasks, infected with virus at an MOT of 3, were pooled, spun down and re-suspended in 10 ml Dulbecco's PBS (Gibco). An equal volume of ARKLONE P™ was added, the cells vortexed thoroughly and then spun for 20 minutes at 15000 rpm. The top layer was then careflly removed and aliquoted into cryo-vials for storage at −70°.

Adenovirus titration is used to calculate the MOI of the viral stock. 69 wells of a 96 well plate are plated with $8 \times 10^4$ 293 cells per well. After 24 hours incubation at 37°, 5%$CO_2$, triplicate serial dilutions of virus in 100 ml, ranging from $10^{-2}$ to $7.63 \times 10^{-12}$, are used to replace the medium. The virus is circulated every 15 minutes for 90 minutes to ensure even distribution. After a further 24 hours incubation another 100 μl of fresh medium was added to each well and then at 3 day intervals the medium is replaced. The wells are monitored daily for plaque formation and after ~8 days of infection the last well with evidence of plaque formation identified and the pfu/ml calculated.

Southern Blot analysis can be used to confirm recombinant adenoviruses, using the Digoxygenin DNA labelling and detection kit (Boehringer Mannheim). The viral DNA containing agarose gel is rinsed with water and then soaked in 0.25M HCl on a shaker for 30 minutes to fragment the DNA. The gel is then soaked in 0.4M NaOH on a shaker for 20 minutes to denature the DNA. Overnight blot transfer of the DNA onto a nitrocellulose membrane is carried out using a suitable transfer apparatus arrangement in FIG. X Following the overnight transfer the membrane is soaked in 5×SSC (0.75M Na Cl; 750 mM Na-Citrate pH 7) briefly and then transferred to a plastic bag. Pre-hybridisation solution (5×SSC; 1% blocking reagent; 0.1% N-laurylsarcosine) is added to the bag, which is sealed without any air bubbles and incubated at 68' for 1–2 hours.

DNA probe preparation and labelling is performed by excision of the transgene cassette from the shuttle plasmid. 5 μg of plasmid DNA is cut and run on a 1% agarose gel to isolate the released cassette fragment. The DNA fragment is recovered from the gel and labelled. Labelling of the Southern probe uses the Digoxygenin DNA labelling and detection kit (Boehringer Mannheim). 1–3 μg of isolated probe DNA is heated for 10 minutes at 95° and then immediately cooled on ice/NaCl. To the microfuge tube 2 μl dNTP mix (Boehringer Mannheim), 2 μl hexanucleotide mix (Boehringer Mannheim), 1 μl Klenow enzyme (Boehringer Mannheim) and distilled water to a final volume of 20 μl is added. This mixture is incubated at 37° for 20 hours after which the reaction is stopped with 2 μl 0.2M EDTA. Labelled DNA is then precipitated with 2.5 μl 4M LiCl and 75 μl cold 70% (v/v) ethanol at−20° for 2 hours. The precipitated DNA is spun down, washed in 70% (v/v) ethanol, air dried and re-suspended in 50 μl distilled water. The membrane is removed from the water bath, the labelled probe added and the bag re-sealed before incubating at 68° overnight. The following day the membrane is washed at room temperature for 15 minutes on a shaker in 2×SSC/ 0.1% SDS. This step is then repeated using 0.2×SSC/0.1% SDS before a final wash in 0.1×SSC/0.1% SDS at 65° for 30 minutes. The filter is then ready for irunnodetection. The filter is washed in bufferl (100 mM Tris-HCl; 150 mM NaCl, pH7.5) for 1 minute followed by a 30 minute incubation in buffer 2 (100 mM Tris-HCl; 150 mM NaCl; 1% blocking reagent pH 7.5). The filter is washed in buffer 1 for a further minute followed by a 30 minute incubation in DIG(AP)-conjugate (Boehringer Mannheim) diluted to 150U/ml in buffer 1. A further 30 minute incubation in buffer 1 takes place followed by 2 minutes of equilibration in buffer 3 (100 mM Tris-HCl; 150 mM NaCl; $MgCl_2$ pH9.5)). The filter was then placed in freshly prepared colour substrate containing 45 μl NBT solution, 35 μl X-phosphate solution and 10 ml buffer 3, in the dark, until bands develop. The colour reaction is then stopped by washing in buffer 4 (10 mM Tris-HCl; 1 mM EDTA pH 8.0) for 5 minutes.

ARKLONE P™, a chlorofluorocarbon that disrupts membrane lipids and thus lyses cells, was obtained from ICI Chlor-Chemicals.

In vivo quality adenovirus stocks are prepared from frozen ARKLONE™ purified virus by CsCl gradient purification. The first CsCl gradient is prepared in a Beckman 14 ml centrifuge tube (Cat No. 331374) by layering 2.5 ml of 1.33 g/ml CsCl solution (8.349 g C Cl, Promega H5331; 16 ml 5M trizma hydrochloride; 1 mM EDTA pH 7.8) over 1.5 ml 1.45 g/ml CsCl solution (8.349 g CsCl; 11.4 ml 5 mM trizma hydrochloride; 1 mM EDTA pH 7.8). ARKLONE™ purified virus is placed onto the gradient over which mineral oil is layered to the top of the tube. The gradient is then ultracentriflged for 2 hrs, 4°, 22,500 rpm. in a swing out rotor. The viral band is the lowest band visible within the gradient and is removed and placed onto a second gradient. The second gradient comprises 1.5 ml of 133 g/ml CsCl solution over 1 ml of 1.45 g/ml CsCl solution. Once again the virus solution is overlayed with mineral oil and the gradient spun for 18 hrs, 4°, 23,800 rpm. The viral band is recovered and dialysed twice against 1 liter Buffer A (10 mM Tris pH 7.5; 1 mM MgCl; 135mM NaCl) for 1 hr and once against 1 liter buffer B (10 mM Tris pH 7.5; 1 mM MgCl; 135 mM NaCl; 10% glycerol). The Cs Cl gradient purified virus is then aliquoted and stored frozen at n70° C.

Viral DNA is extracted directly from a 10 μl CsCl purified frozen stock by adding 100 μl extraction buffer 20 mM Tris HCl pH 7.8; 10 mM EDTA; 1% SDS; 1 mg/ml proteinase K and incubated for 2 hrs, 37°. The DNA is extracted twice with an equal volume of phenol/chloroform/isomyl alcohol (25:24:1) and is then precipitated with 2 volume of ethanol.

Quality control of in vivo grade adenovirus preparations is achieved by testing $10^9$ pfu of each adenovirus preparation. for contaminating replication competent adenovirus particles using methodology adapted from Dion L. D. et al. J Virological methods (1996) 56, 99–107. $6 \times 10^6$ Hela cells/ plate seeded into 6×10 cm petri dishes are infected with $1.8 \times 10^8$ pfu/4 mls DMEM; 2%FCS/plate. 6 hrs later a further 4 ml DMEM; 2%FCS is added and the cells left for 3 days. The media is then removed, centrifuged and 300 μl from each plate placed in triplicate onto a secondary plate previously seeded with $5 \times 10^4$ Hela cells/well. 6 hrs later the media is replaced with 500 μl DMEM, 2%FCS. The plate is observed for 6 days. If no evidence of CPE is observed the RCA contamination in the virus preparation is below 1 RCA in $10^9$ pfu of replication defective virus.

To test for the prescence of Gram negative bacterial endotoxin in the in vivo grade adenovirus preparations a qualitative Lirnulus Amebocyte Lysate test is used (Pyrogen® Cat No N183, N184).

The virus particle concentration of each adenovirus preparation is calculated by measuring optical density at 260 nm using a methodology taken from Mittereder, N. et al. J. Virol (1996), 7 7498–7509. 10 ml of in vivo grade virus is diluted with 190 μl virion lysis solution (0.1% SDS; 10 mM Tris-HCl pH 7.4; 1 mM EDTA) and incubated for 10 min at 56°. The solution of disupted virions is then placed in a quartz cuvette and $OD_{260}$, $OD_{260}$ measurements taken using a UV spectrophotometer.

Cytotoxicity assay incorporating recombinant adenovirus cell transfection and subsequent expression of transgene protein. LoVo cells are plated out in to 96 well plates (Biocoat plates, poly-L-lysine coated, Becton Dickinson 35–6461(50)) at concentration of either $3×10^3$ cells per well (or alternatively $1×10^2$, $5×10^2$ or $1×10^3$ cells per well and incubated overnight at 37° C. The next day, the media is carefully removed from all wells and add 100 µl fresh complete DMEM containing folinic acid (1 µg/m/) added. Following this the adenoviral stock solution is diluted in complete DMEM containing folinic acid to the desired MOI and added to the appropriate wells in total volume of 100 µl. The plates are then incubated at 37° for 48 hours to allow for adeonoviral gene expression. Following incubation, the supernatant is removed and the cells washed twice with 200 µl fresh DMEM, add 100 µl complete DEM containing folinic acid to each well. The chosen prodrug is then prepared at the appropriate dilutions in media and added to the wells in total volume of 100 µl. The cells are incubated with the prodrug for for 1 hour at 37° after which the media is removed and replaced with 200 µl fresh complete DMEM with folinic acid. Following incubation for 4 days to allow cell proliferation, 50 µl of an ice cold 50% TCA solution is added to each well (final well concentration: 10%) and incubated at 4° for 1 hour. The plates are then washed 5× with water and 100 µl of SRB dye (0.4% in 1% acetic acid) added to the appropriate wells and incubated for 30 mins at room temperature (as described by Skehan et al J.Natl Cancer Inst. 82, 1107, 1990). The plates are washed 5× with a 1% acetic acid solution and the plate allowed to completely dry at room temperature (1–2 hrs). Finally, 100 µl of 10 mM Tris pH7.5 solution is added, the plate agitated for 30 mins and then read at OD 540nm in a suitable 96 well plate reader.

AstraZeneca prodrug ZD2767P (molecular weight 590.15) is prepared by dissolving 29.5 mg in 5001 µl dimethylsulphoxide (DMSO) giving a 100 mM stock. This stock is diluted in the appropriate cell culture media to produce the dosing concentration required and used immediately.

Microorganism deposits: Plasmid pNG3-Vkss-HuCk was deposited at The National Collections of Industrial and Marine Bacteria (NCIMB), 23 St Machar Drive, Aberdeen AB2 IRY, Scotland, United Kingdom on 11, Apr. 1996 under deposit reference number NCIMB 40798 in accordance with the Budapest Treaty. Plasmid pNG4VHss-HulgG2CH1' was deposited at The National Collections of Industrial and Marine Bacteria (NCIMB), 23 St Machar Drive, Aberdeen AB2 1RY, Scotland, United Kingdom on 11, Apr. 1996 under deposit reference number NCIMB 40797 in accordance with the Budapest Treaty. Plasmid pNG3-Vkss-HuCk-NEO was deposited at The National Collections of Industrial and Marine Bacteria (NCIMB), 23 St Machar Drive, Aberdeen AB2 1IRY, Scotland, United Kingdom on 11, Apr. 1996 under deposit reference number NCIMB 40799 in accordance with the Budapest Treaty. Plasmid pICI266 was deposited under accession number NClMB 40589 on 11, Oct. 93 under the Budapest Treaty at the National Collections of Industrial and Marine Bacteria Limited (NCIMB), 23 St. Machar Drive, Aberdeen, AB2 IRY, Scotland, U.K

EXAMPLE 1

Construction of a GPI Anchored CPG2 Protein

To allow evaluation of both potentially glycosylated and Q3 variants of CPG2 (both with and without an added GPI anchor) in mammalian cell expression systems, a clining strategy was planned so that four different CPG2 gene variants could be easily cloned and expressed.

To this end, genes were constructed which expressed secretable forms of glycosyl and Q3 variant CPG2 as well as the corresponding GPI anchored forms. In each case the gene construct was designed to encode a 5' secretory leader sequence (a kappa antibody light chain signal sequence—Vkss). On expression, the encoded protein would be directed to leave the cell, and as it passed through the cell membrane, the leader sequence cleaved.

a) Generation of the Synthetic CPG2 Gene

The nucleotide coding sequence for CPG2 has been published by Minton, N. P. et al., Gene, (1984) 31, 31–38 and the crystal structure has been determined by Rowsell, S. etal., Structure. (1997), 5, 337–347, therefore the CPG2 gene may be produced as a synthetic cDNA construct by a variety of methods. Total gene synthesis has been described by Edwards, M., Am. Biotech. Lab. (1987), 5, 38–44, Jayararnan et al. Proc. Natl. Acad. Sci. USA (1991), 88, 4084–4088, Foguet and Lubbert, Biotechniques (1992), 13, 674–675 and Pierce Biotechniques. (1994), 16, 708. The synthetic CPG2 gene was sequenced within the pBLUESCRIPT™ plasmid to confirm the CPG2 cDNA sequence (SEQ ID NO: 1). This sequence is identical to the natural bacterial enzyme sequence except for 1 b.p. change, allowing a restriction site to be removed, to ease the planned cloning strategy. This change is a silent mutation with no affect on the encoded amino acid sequence of the CPG2 protein (SEQ ID NO: 2).

b) Preparation of the Vector for Synthetic CPG2 Gene Cloning

In preparation for cloning of the synthetic CPG2 gene, a simple derivative of the plasmid pNG3-Vkss-HuCk-NEO (NCIMB deposit no. 40799) which contains a neomycin resistance gene) was made. The neomycin gene was excised to remove an EcoRl restriction site which would have caused cloning difficulties, by Xba 1 digestion of the aforementioned plasmid. The vector fragment was isolated and the vector re-ligated to form the plasmid pNG3-Vkss-HuCk (NCIMB deposit no. 40798).

This vector was digested with the enzymes SacII and EcoRI, to excise the HuCk gene fragment that encodes an unwanted human antibody light chain kappa constant domain and prepare for cloning of the synthetic CPG2 gene. The restriction fragments were separated by agarose gel electrophoresis and the vector band excised, purified and dephosphorylated.

c) Cloning of the Synthetic CPG2 Gene into pNG3-Vkss-HuCk

The CPG2 structural gene encoding amino acid residues Q26-K415 inclusive (of the wild type protein sequence) was amplified by PCR, using the pBLUESCRIPTI/CPG2 plasmid as a DNA template and the synthetic oligonucleotide primers CME00226 (SEQ ID NO: 3) and CME03709 (SEQ ID NO: 4) which include a 5' Sacl restriction site and a 3' EcoRI restriction site to allow directional, in frame cloning into the prepared vector. Standard PCR reaction conditions were used and the product analysed using a 1% agarose gel. A band of expected size, approx. 1200 b.p., was excised and purified. This material was then digested with SacII and EcoRI and the resultant fragment ligated into the prepared vector. The ligation mix was transformed into E.coli and ampicilin resistant clones analysed for the prescence of the CPG2 gene by DNA restriction analysis using SacII and EcoRI. Clones containing a fragment of the correct size were confirmed by sequencing. The plasmid was sequence and named pNG3/RC/CPG2. The gene and encoded protein sequence for the synthetic CPG2 structural gene with the 5" addition of the kappa light chain secretory leader sequence is shown in (SEQ ID NO: 5 and 6).

d) Construction of the CPG2(Q3) Variant

Since this bacterial enzyme encodes 3 potential N-linked glycosylation sites when expressed from mammalian cells, a mutation strategy was designed to allow modification of the recognition sites to remove the potential for such glycosylation.

The plasmid pNG3/RC/CPG2 was used as a template for the PCR mutagenesis of the synthetic CPG2 gene. The putative amino acid glycosylation sites (N-X-T/S) were observed at positions 222–224 (N-I-T), 264–266 (N-W-T), and 272–274 (N-V-S) using the positional numbering published by Minton, N. P. et al., in Gene, (1984) 31, 31–38. The asparagine residue (N) of the 3 glycosylation sites was mutated to glutamine (Q) thus negating the glycosylation recognition sites to avoid any potential glycosylation events.

A PCR mutagenesis technique in which all 3 sites are mutated in a single reaction series was used to create the CPG2(Q3) variant. The vector pNG3/RC/CPG2(N3) was used as a template for three initial PCR reactions. Reaction R1 used synthetic oligonucleotide primers CME00226 and CME00398 (SEQ ID NO: 3 and 7), reaction R2 used synthetic oligonucleotide primers CME00226 and CME00399 (SEQ IID NO: 3 and 8), and R3 used synthetic oligonucleotide primers CME00400 and CME03709 (SEQ ID NOS: 9 and 4). The products of PCR reactions R1 and R2 contained the mutated 222 and 264+272 glycosylation sites respectively, with the R3 product being a copy of the C-terminal segment of the CPG2 gene. The R2 and R3 products (R2 approximately 750 b.p. and R3 approximately 360 b.p.) after agarose gel separation and purification were joined in a further PCR reaction using equal amounts of each as the template. Reaction R4 used the synthetic oligonucleotide primers CME00226 and CMB03709 (SEQ ID NO: 3 and 4),. The R4 product (R4 approximately 1200 b.p.) was used as the template in the PCR reaction R5 using the synthetic oligonucleotide primers CME03709 and CME00398 (SEQ ID NO: 4 and 7). The resulting product RS (R5 approximately 600 b.p.) and product R1 were used in a final joining PCR reaction R6 performed using the synthetic oligonucleotide primers CMB00226 and CME03709 (SEQ ID NO: 3 and 4). This fnal R6 product (R6 approximately 1200 bp), which now contained all three mutated glycosyladon sites, could be digested with Agel and EcoRI and the resultant fragment isolated and ligated into the vector pNG3/RC which had been previously linearised by digestion with AgeI and EcoRI. The ligation mix was transformed into *E.coli*. DNA was prepared from the clones obtained and subsequently sequenced to confirm that all three glycosylation sites of the CPG2 had been mutated (SEQ D NO: 10). This created the desired CPG2(Q3) cDNA sequence within the expression vector pNG3/RC/CPG2(Q3). This plasmid encodes the Q3 variant, secreted form of the CPG2 protein (SEQ ID NO: 11).

e) Construction of the CPG2-Thy 1 Gene Variants

For addition of a GPI anchor to either the glycosylatable or Q3 forms of the CPG2 enzyme the last exon of the rat brain antigen Thy 1 gene was linked in frame via a proline codon to the C-terminus of the appropriate CPG2 gene (FIG. 1). This last exon of Thy 1 encodes the carboxy terminal 37 amino acids of the Thy 1 protein which provide the signal for post translational GPI anchor addition to the protein in the endoplasmic reticulum. The last 31 ammno acids of Thy 1 are cleaved within the endoplasmic reticulum and replaced by the addition of a GPI anchor to the carboxyl terminus of the protein via an amide bond. The naturally secreted protein, tissue inhibitor metalloproteinase (TIMP) has been successfully GPI anchored in vitrn, using this method by Clissold, P. M., J.Biochem. (1992) 281, 129–136. The amino acid sequence of the last exon of Thy 1 which conferred the property of GPI anchorage onto TIMP was determined by Clissold, P. M., I.Biochem. (1992), 281, 129–136 (SEQ ID NO: 12). Using this Thy 1 amino acid sequence, a cloning strategy was designed to allow an appropriate DNA sequence encoding this last Thy 1 exon to be cloned in fiame at the 3' end of either CPG2 or CPG2(Q3) genes (FIG. 3). The designed coding sequence was added by a two step cassette mutagenesis strategy (FIG. 1). Firstly, two synthetic oligonucleotides CME 4052 and CME 4053 (SEQ ID NO: 13 and 14) were annealed together to produce a double stranded DNA cassette Thy 1A. Thy 1A encoded the CPG2 3' end sequence separated from the 5' Thy 1 sequence by a single proline codon and also introduced a unique NheI restriction site, to facilitate the cloning of the second DNA cassette. The Thy 1A cassette which carried intrinsic 5' BsrGI and 3' EcoRI restriction enzyme cohesive ends was ligated into the appropriately restricted and prepared pNG3/RC/CPG2(Q3) vector. The ligation mnix was transformed into *E.coli* and clones were confirmed by digestion with Nhel (which linearised positive clones). This intermediate plasimid pNG3/RC/CPG2(Q3)-Thy 1A was digested with the restriction enzymes NheI and EcoRI after which the DNA was dephosphorylated and the large vector band separated from the small NbeI/EcoRI fragment and purified.

A second pair of synthetic oligonucleotides, CME 4054 and CME 4055 (SEQ ID NO: 15 and 16) were annealed together to produce the DNA cassette Thy 1B. Thy 1B encodes the residual 3' Thy 1 sequence terminated by two stop codons. This cassette which carried intrinsic 5' NheI and 3' EcoRI cohesive ends was ligated into the prepared pNG3/RC/CPG2-(Q3)Thy 1A plasmid to construct the plasmid pNG3/RC/CPG2(Q3)Thy 1 which was confirmed by sequencing (SEQ ID NO: 17).

The same strategy was used to construct the plasmid pNG3/RC/CPG2-Thy 1, substituting the plasmid pNG3/RC/CPG2 for pNG3/RC/CPG2(Q3). Again the final plasmid was confinmed by sequencing (SEQ ID NO: 18).

f) Transient Expression

The two plasmids pNG3/RC/CPG2 and pNG3/RC/CPG2 (Q3) (which encoded the glycosylatable and Q3 variant secretory forms of the CPG2 protein respectively) were transfected into COS-7 cells using the LIPOFECTIN™ transfection procedure. To confirm that the mutagenesis of CPG2 to CPG2(Q3) had removed all potential glycosylation sites, the two proteins were also expressed in the presence of the glycosylation inhibitor, tunicamycin. After 72 h of expression the cell supernatants were harvested for analysis.

The remaining two plasmids pNG3/RC/CPG2-Thy 1 and pNG3/RC/CPG2(Q3)-Thy 1, (which encoded the glycosylatable and unglycosylated GPI anchored CPG2 proteins respectively) were also transfected into COS-7 cells using a LIPOFECTIN™ based procedure. After 72 h of expression the cell supernatants were removed and assayed, and the remaining adherent cells washed with PBS, then trypsinised and analysed.

g) Analysis of Secreted CPG2 Protein

The supernatant material was analysed for the presence of secreted CPG2 protein using SDS/PAGE followed by Western blotting. To measure CPG2 enzyme activity, HPLC based CPG2 enzyme activity assay was employed and the described CPG2 capture ELISA was used to quantify the amount of secreted CPG2 protein present within the crude supernatant samples. For the three types of analysis, purified, bacterially expressed, CPG2 was used as a standard (Sigma C4053).

The HPLC based enzyme activity assay confirmed that CPG2 enzyme activity was present in all of the cell supernatants. The CPG2 activity measured for the secreted CPG2 constructs was approximately 50 fold greater than that expressed from the GPI anchored CPG2 constructs. The presence of some low level activity measured for the GPI anchored CPG2 constructs may be due to cleavage of GPI anchored CPG2, cell lysis and release of internal CPG2 enzyme within the secretory pathway or inefficient post translational modification leading to non recognition of the GPI signal sequence.

Figure 1:
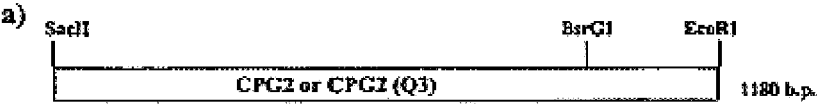
FIG. 1 shows the cassette mutagenesis strategy for Thy 1 sequence addition, in frame, at the 3' end of CPG2 and CPG2(Q3). (a) shows restriction sites in CPG2 (NB there are 2 stop codons at the 3' end—not shown); (b) shows Thy 1 A insertion; (c) shows Thy 1 B insertion; (d) shows the final CPG2-Thy 1 construct (NB there are 2 stop codons at the 3' end and a proline is encoded at the CPG2/Thy 1 junction-not shown).
Figure 1:
Figure 1:
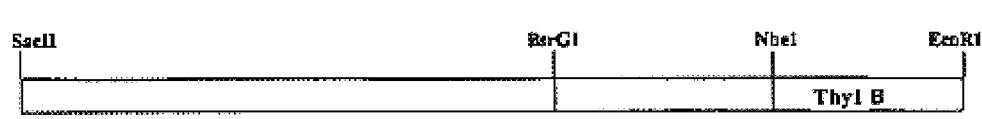
Figure 1:
Figure 2:
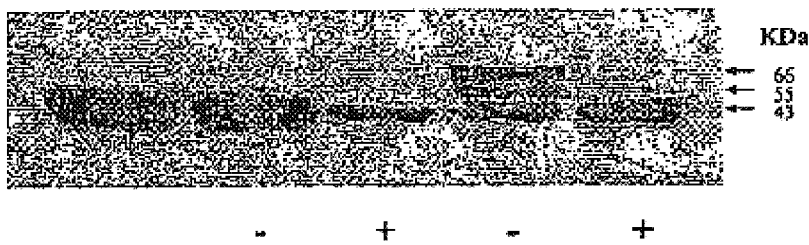
FIG. 2 shows western blot analysis to detect secreted CPG2 protein, performed upon crude cell supernatants, taken from COS 7 cells transiently transfected with either pNG3/RC/CPG2 or pNG3/RC/CPG2(Q3), in the prescence or absence of 10 µg/ml tunicamycin. The blot shows that expression of the secreted form of CPG2 gives a distinct pattern of three different CPG2 protein products. The smallest band has the same mobility as bacterial CPG2 (43 k Da)

Western blot analysis showed that expression of the secreted form of CPG2 gave a distinct pattern of three different CPG2. protein products (FIG. 2). The smallest band had the same mobility as bacterial CPG2 therefore is most likely unglycosylated CPG2 indicating that the glycosylation process within the COS 7 cells was not 100% efficient. A subunit of bacterial CPG2 has a molecular weight of 41,800 Da determined by Rowsell, S., et al. Structure. (1997) 5, 337–347, when sized against a high molecular weight marker, the bacterial CPG2 on the SDS/PAGE gel ran at approximately 43 KDa These two larger bands probably represented glycosylated CPG2 forms. The largest band had an approximate size of 66 KDa and the middle band 55 KDa Tunicamycin addition completely blocked glycosylation of CPG2, with Western analysis showing the expression of the single 43 KDa band representing unglycosylated CPG2 protein. Supematant analysed from CPG2(Q3) expression gave a single band of 43 KDa, the mobility of which was unaffected by tunicamycin, proving that the mutagenesis of the three asparagine residues to glutamine residues had resulted in the expression of a uniform Q3 variant of the CPG2 protein.

The specific activity of the unpurified CPG2(Q3) protein present within the crude supernatant samples was calculated by correlating the total CPG2 protein ELISA results and enzyme activity data for CPG2(Q3) and comparisons made with the specific activity of purified bacterial CPG2 which is 500 units/mg. The specific activity of the unpurified CPG2 (Q3) protein was approximately 5 fold lower than its wild type bacterial enzyme at 71–120 units/mg. This remained essentially unchanged when CPG(Q3) was expressed in the prescence of tunicamycin and a specific activity of 90–124 units/mg was recorded. From these crude supernatant samples it was not possible to calculate accurately the specific activity of glycosylated CPG2 alone, as the previous Westem analysis had shown that three CPG2 protein forms were present within these samples. However, the combined specific activity of these three CPG2 protein forms was 61–87 units/mg which surprisingly indicates significant activity of CPG2 when glycosylated (in contrast with reported inactivity of glycosylated CPG2 in WO 96/03515; see page 39, lines 18–20). Western analysis bad also shown that in the prescence tunicamycin only one of these protein forms was expressed, the unglycosylated CPG2 protein. The specific activity of this CPG2. protein was 165–210 units/mg indicating that mutagenesis of the CPG2 gene to CPG2 (Q3) had reduced the activity of the expressed enzyme by only 2 fold compared with bacterial expressed enzyme.

h) Analysis of GPI Anchored CPG2 Protein

Transiently transfected COS 7 cells were analysed by FACS to detect cells with membrane associated CPG2 protein when either the CPG2-Thy 1 or CP02(Q3)-Thy 1 genes were expressed in COS7 cells. Untransfected cells and cells secreting CPG2 and CPG2(Q3) were used as negative controls. For both CPG2-Thy 1 or CPG2(Q3)-Thy 1 approximately 8% of cells were displaying CPG2 compared to a maximum background of 2%.

The CPG2 capture ELISA assay can only be used to measure free CPG2 protein concentration therefore could not be used to measure the concentration of GPI anchored CPG2 protein attached to the COS 7 cell membrane, consequently specific activity data could not be generated for either of the two GPI anchored CPG2 proteins using this methodology.

EXAMPLE 2

Replication Defective E1/E3 Deleted Adenovirus Vector Construction

To explore the effects produced with each of the four described forms of CPG2 when utilising adenoviral delivery, four individual replication defective E1/E3 deleted Adenovirus serotype 5 (RAd) vectors were constructed RAd/CPG2 expressing the glycosylatable CPG2 secreted protein; its GPI anchored form RAd/CPG2-Thy 1; RAd/CPG2(Q3) expressing the mutated, unglycosylated secreted CPG2 protein and its GPI anchored form RAd/CPG2(Q3) Thy 1.

RAd vector generation was achieved using a two plasmid methodology followed by homologous recombination in eukaryotic cells (see Mittal, S. K et al., Virus Res. (1993) 28, 67–90 and Stratford-Perricaudet, L. D. et al., J. Clinical. Invest. (1992) 9Q, 67–90). Similarly, an alternative strategy for homolgous recombination in bacteria may also be used (Tong-Chuan He, et al., Proc. Natl. Acad. Sci. USA (1998) 95, 2509–2514).

The transgene is cloned either within, or into an expression cassette, in a shuttle plasmid. This shuttle plasmid is cotransfected with a second plasmid encoding the complete Ad5 genome, but with a prokaryotic sequence inserted into the El region making the plasmid too large for packaging into a replicative virus.

The plasmids are cotransfected into a 293 human kidney packaging cell line, immortalised by Graham, F. L et al., J. Gen. Virology (1977) 36, 59–72, to constitutively express the viral proteins E1A and E1B. Following cotransfection, intraceuular homologous recombination between overlapping fragments within the two plasmids, results in the replacement of the E1 region and prokaryotic sequence with the cDNA cassette containing the transgene. This reduces the size of the Ad5 viral genome to a packageable size, and with the production of the E1 viral proteins in trans, replication occurs allowing high titers of virus to be produced.

a) Shuttle Plasmid Gloning

The shuttle plasmid pΔE1sp1A was obtained from Microbix Biosystems Inc, Canada A simple cloning strategy was then employed to clone the four CPG2 cDNA cassettes (FIG. 3), contained within the plasmid pNG3/RC created in Example 1, into this shuttle plasmid. In preparation for the cloning of a CPG2 gene cassette into the multiple cloning site of pΔE1sp1A the plasmid was digested with the restriction enzymes XbaI and BglII. After dephosphorylation, the vector fragments were separated by agarose gel electrophoresis and the remaining vector backbone fragment excised and purified. The CPG2 gene cassette was excised from appropriate pNG3/RC plasmid using the restriction enzymes XbaI and BglII and the fragment of approximately 2.3 Kb isolated, ligated into the prepared pΔE1sp1A vector and used to transform *E.coli*. Positive clones were confirmed by restriction enzyme digest by re-excision of the gene cassette with the above mentioned enzyvnes. This process was performed for each of the four different CPG2 cDNA cassettes using the pertinent pNG3/RC vector as the source for each of the cassettes. Thus four shuttle plasmids were assembled pΔE1sp1A/CPG2, pΔE1sp1A/CPG2(Q3), pΔE1sp1A/CPG2-Thy 1 and pΔE1sp1A/CPG2(Q3)Thy 1.

b) Cotransfection and Viral DNA Verification 293 cells were cotransfected with the shuttle plasmid pΔE1sp1A/CPG2 and the Ad5genome plasmid pJM17 (Microbix Biosystems Inc, Canada) using the calcium phosphate cotransfection method. CPG2 is potentially toxic to the 293 cells as it depletes folic acid. To counteract any depletion, folinic acid supplemented (FAS) media was used following cotransfection. Cells showing cytopathic effect (CPE) were harvested. To confirm that the correct recombination event had occurred, resulting in the generation of pΔE1sp1A/CPG2, viral DNA was extracted from each positive flask of cells exhibiting CPE. The viral DNA was digested to produce two banding patterns. Firstly with the restriction enzymes BglII and XbaI to release the whole CPG2 cassette and secondly with Hind III alone. The digestion reaction products were separated by agarose gel electrophoresis and the two banding patterns compared with the expected patterns.

To identify the virus conclusively, a Southern blot analysis of the separated fragments was carried out. A probe was prepared from the CPG2 gene cassette by excision of the whole cassette from pΔE1sp1A/CPG2 with the restriction enzymes BglII and XbaI. The cassette fragment was isolated by agarose gel electrophoresis, purified and labelled following the digoxygenin DNA labelling method. The probe hybridised to the correct bands within the RAd/CPG2 Southern blot verifying its identity. As expected, the probe hybridised to the CPG2 cassette fragment (size 2312 b.p.) when the BglII/XbaI digestion products were probed and similarly, to two fragments of sizes 3954 and 1791 b.p. when a HindIII digestion products were probed. Cotnasfection, followed by verification of the virus, was repeated with the shuttle plasmid pΔE1sp1A/CPG2(Q3). Using the CPG2(Q3) gene cassette, BglII/XbaI fragment as a probe, the same banding pattern and Southern blot as for RAd/CPG2 was seen, corfinning the virus as RAd/CPG2(Q3).

Furthermore, RAd/CPG2-Thy 1 and RAd/CPG2(Q3)-Thy 1 viral constructs were prepared in the same way using pΔE1sp1A/CPG2-Thy 1 and pΔE1sp1Ap/CPG2(Q3)-Thy 1 respectively in the cotransfection. Upon Southern blot analysis of the viral DNA the correct banding and hybridisation pattern for both viruses was seen. The CPG2 or (CPG2 (Q3)-Thy 1) gene cassette was excised by BglII/XbaI digestion of pΔE1sp1A/CPG2 or (CPG2(Q3)-Thy 1) then labelled. This probe hybridised to the CPG2 or (CPG2 (Q3)) cassette fragment (size 2312 b.p.) when the BglII/XbaI digestion products were probed and similarly, to two fragments of sizes 3954 and 1893 b.p. when the HindIII digestion products probed.

c) Adenovirus Vector Purification

The four viruses RAd/CPG2, RAd/CPG2(Q3), RAd/CPG2-Thy 1 and RAd/CPG2(Q3)-Thy 1, were purified and the virus stock titrated as described above.

d) Adenovirus Vector Expression

ARKLONE P™ purified stocks of the four RAd vectors RAd/CPG2, RAd/CPG2(Q3), RAd/CPG2-Thy 1 and RAd/CPG2(Q3)-Thy 1 were used to infect CHO K1 (chinese hamster ovary) cells. The supernatant was harvested for analysis 48 hours after infection.

e) Analysis of Secreted CPG2 Protein Expressed from Infected CHO K1 Cells

The supernatant material from adenovirally infected CHO K1 cells was analysed for the presence of secreted CPG2 protein by measuring the CPG2 enzyme activity using the HPLC based CPG2 enzyme activity assay. A CPG2 capture ELISA was used to quantify the amount of secreted CPG2 protein and from this an estimation of the specific activity of each form of unpurified CPG2 protein could be calculated, allowing a comparison of virally expressed CPG2 enzyme activity with that of the plasmid expression calculated in example 1.

The HPLC based enzryme activity assay confirmed that CPG2 enzyme activity was present in all of the cell supematants. The CPG2 activity expressed from the secreted CPG2 constructs was approximately 100 fold greater than that expressed from the GPI anchored CPG2 constructs as expected.

Virally expressed secretable CPG2 and CPG2(Q3) had specific activity of 71 units/mg and 180 units/mg respectively which is comparable to the specific activity calculated for these enzymes when tnansiently expressed from plasmid constructs.

f) Analysis of GPI Anchored CPG2 Protein Expression in MDCK Cells

In addition, ARKLONE P™ purified stocks of the four RAd vectors RAd/CPG2, RAd/CPG2(Q3), RAd/CPG2-Thy1 and RAd/CPG2(Q3)-Thy1 were used to infect MDCK epithelial cells and after 48 hours expression both the supernatant and the intact cells were analysed.

MDCK cells are polarized, exhibiting an apical and basolateral membrane. GPI membrane anchoring has been shown to act as a targeting signal for protein expression on the apical side of these polarized epithelial cells (Lisanti, M. P. and Rodriguez-Boulan. E., Trends Biochem. (1990) 15, 113–118) irrespective of whether it is an endogenous protein or a recombinant protein; with such a signal engineered onto its carboxy terminus. Expression of RAdlCPG2-Thy 1 and RAd/CPG2(Q3)-Thy 1 in these cells allowed apical targeting of the two GPI anchored CPG2 proteins.

The MDCK cells were analysed using immunocytochemical (ICC) staining for both intracellular and membrane targeted CPG2. MDCK cells infected with either vectors RAd/CPG2 or RAd/CPG2(Q3), expressing secreted CPG2, showed strong endoplasmic reticulum staining when permeabilised but no CPG2 detection when unpermeabilised. In contrast cells infected with RAd/CPG2-Thy 1 or RAd/CPG2(Q3)-Thy 1, expressing GPI anchored CPG2 protein again exhibited strong endoplasmic reticulum staining when permeabilised but a punctate staining pattern, indicative of apical membrane display, when the cells were unpermeabilised. Further evidence that the CPG2 protein was GPI anchored was achieved by CPG2 cleavage from the surface of the cells using phosphatidylinositol phospholipase C (PI-PLC). FACS analysis was employed pre and post treatment to detect loss of membrane associated CPG2. The results showed that treatment with PI-PLC cleaved 85% of GPI anchored CPG2 and 62% of GPI anchored CPG2 (Q3) which clearly indicated that both CPG2 forms were displayed at the cell surface and retained via GPI anchoring.

In addition, when GPI anchored proteins are cleaved from a cell membrane by the enzyme PI-PLC, the released protein retains a small part of the GPI anchor, termed the cross reacting determinant (CRD). This GPI epitope is specifically recognised by the CRD antibody. Western blot analysis of the supernatant samples containing the cleaved GPI proteins, using detection with this CRD antibody, confirmed that a 43 KDa protein (the approximate size of CPG2) had been cleaved from the MDCK cells and released into the surrounding supematant.

EXAMPLE 3

Generation of CHO K1 Stable Cell Lines

To facilitate in i cytotoxicity studies, four stable cell lines were generated to express each form of CPG2. Cell lines were generated which expressed secretable forms of glycosylatable or Q3 variant CPG2 as well as the corresponding GPI anchored forms.

a) Insertion of the Neomycin Resistance Gene into the Four CPG2 Expression Vectors.

To enable selection of stable transfonnants, a selectable neomycin gene was added to the CPG2 expression vectors described in Example 1. The plasmid pNG3-VkssHuCk-NEO (NCIMB deposit no. 40799) was used as a source for the NEO gene. This plasmid was digested with XbaI to excise the neomycin gene which was isolated from the digestion products by agarose gel electrophoresis and purified. To prepare pNG3/RC/CPG2 to receive the neomycin gene the plasmid was linearised with XbaI and dephosphorylated. The neomycin gene was ligated into pNG3/RC/CPG2 to produce the required plasmid pNG3/RC/CPG2/NEO. This process was repeated for each of the other 3 CPG2 expression vectors using the pertinent vector as the starting vector.

b) Stable Transfectin

The two plasmids pNG3/RC/CPG2/NEO and pNG3/RC/CPG2(Q3)/NEO (which encoded the glycosylatable and Q3 secretory forms of the CPG2 protein respectively) were transfected into CHO K1 cells using the stable LIPOFECT-INMT transfection procedure and stable clones selected using 1.5 mg/ml G148 selection.

The remaining two plasrnids pNG3/RC/CPG2-Thy 1/NEO and pNG3/RC/CPG2(Q3)-Thy 1/NEO, (which encoded the glycosylatable and unglycosylated GPI anchored CPG2 proteins respectively) were also transfected into CHO K1 cells using the same methodology. The stable cell lines expressing secreted CPG2 may be confirmed by HPLC CPG2 enzyme activity detection and expression of membrane associated GPI anchored CPG2 confirmed by FACS analysis.

EXAMPLE 4

An Expression Vector for Expression of a CPG2 (with Unaltered Glycosylation Sites)-c-erb 2 Transmembrane Region Anchor Hybrid An expression vector for expression of a CPG2-c-erb b2 transmembrane region anchor wherein the CPG2 comprises unaltered glycosylation sites may be prepared according to general experimental details described in WO 96/03515 and Marais et al (1997) Nature Biotechnology 15:1373.

EXAMPLE 5

Pharmaceutical Composition

The following illustrates a representative pharmaceutical dosage form containing a vector of the invention which may be used for therapy in combination with a suitable prodrug.

A sterile aqueous solution, for injection either parenterally or directly into tumour tissue is prepared, containing $10^7$–$10^{11}$ adenovirus particles comprising a vector of the invention as described in Examples 1, 2 or 4.

A second part of a two part pharmaceutical pack comprises a prodrug selected from N-(4-[N,N-bis(2-iodoethyl)amino]phenoxycarbonyl)-L-glutamic acid, N-(4-[N,N-bis(2-cloroethyl)amino]-phenoxycarbonyl)-L-glutamic-gamma-(3,5-dicarboxy)anilide or N-(4-[N,N-bis(2-chloroethyl)amino]-phenoxycarbonyl)-L-glutamic acid or a pharmaceutically acceptable salt thereof. Three×20 ml type 1 glass vials each containing 610 mg of prodrug and three ampoules, each containing 11 ml of 2.15% (w/v) sodium hydrogen carbonate, are used for final dosage form prodrug preparation. Needles (3×18G) and hydrophobic filters for venting the vials and 3× single use sterile 0.22 micron filters for aqueous solutions are also included. All materials must be stored in a fridge (2–8°).

These operations are preferably to be performed under sterile conditions. No more than 1 hour prior to dosing, one vial of prodrug is vented with a needle and hydrophobic filter. Sterile 2.15% w/v sodium hydrogen carbonate (10 ml) is then added directly through the bung via a syringe and needle. With the vent still in place the vial is swirled gently to obtain a clear solution (this will be 50 mg/ml as free base). The required dose volume is withdrawn into a sterile syringe through a sterile filter. The filter is then replaced by a sheathed sterile needle and the syringe unit kept cool prior to administration. Each remaining vial is prepared in an identical manner at intervals of one hour to allow for example three separate doses to be given 1 hour apart.

In use, 3–7 days after administration of vector to a human, three 1 g doses of prodrug are administered as sterile solutions at hourly intervals.

EXAMPLE 6

Preparation of In Vivo Grade E1/E3 Deleted Adenovirus Vector Preparations a) CsCl Gradient Adenovirus Vector Purification The four viruses RAd/CPG2, RAd/CPG2(Q3), RAd/CPG2-Thy 1 and RAd/CPG2(Q3)-Thy 1 were purified by Cs C1 gradient from arklone purified frozen stocks and the resulting in vivo grade virus stocks titrated. Viral DNA was extracted from the four virus stocks and amplified by polymerase chain reaction using synthetic oligonucleotide primers CME06798 (SEQ ID NO: 19) and CME06805 (SEQ ID NO:20) to confirm the presence of a correctly sized trausgene cassette. For RAd/CPG2 and RAd/CPG2(Q3) a PCR product of 1407 b.p. was amplified and for RAd/CPG2-Thy 1 and RAd/CPG2(Q3)-Thy 1 a PCR product of 1521 b.p.

b) Quality Control of Adenovirus Preparations

The in vivo grade virus stocks were tested for contaminating replication competent adenovirus particles using an RCA assay described above and were shown to contain fewer than 1 RCA in $10^9$ E1/E3 deleted adenovirus vector particles. Using a qualitative test for Gram-negative bacterial endotoxin all of the stocks were determined to be negative. Measurement of the optical density at 260 nm, allowing the number of virus particles to be calculated for each of the virus stocks, showed that all of the preparations had at least 1 infection particle for every 20 virus particles.

EXAMPLE 7

Confirmation that GPI Anchored CPG2(Q3) is Functional a) In Vitro Cell Killing Capability of E1/E3 Deleted Adenovirus Vector Delivery of a Prodrug Activating Enzyme Followed by Prodrug Administration LoVo cells were infected with RAd/CPG2(Q3)-Thy 1 or RAd/CPG2(Q3) at various MOIs, to enable cell expression of either GPI membrane anchored secreted or CPG2 protein respectively. After 2 days to allow gene expression, the culture supernatant was removed from the wells and the cells were washed to remove any unbound CPG2 before exposure of the cells to a single dose of ZD2767P. The cytotoxicity and SRB staining was completed using the methodology previously described. The extent of the cytotoxic effect could be assessed by the reduction in OD540 nm absorption reading. From FIGS. 4a and 4b it can be observed that cells transfected with the adenovirus encoding the membrane anchored CPG2(Q3) exhibited increased levels killing in a prodrug dose responsive manner. Meanwhile in the case of cells transfected with the adenovirus encoding the secreted CPG2(Q3) little or no cell killing was observed at the prodrug concentrations used. Since the cells were washed before prodrug addition (to remove any non-cell bound enzyme) and the prodrug ZD2767P does not to any real extent enter the cells, it may be concluded that the cell death observed in the cells transfected with RAd/CPG2(Q3)-Thy 1 was as a result of conversion of ZD2767P to active drug by functional (cell surface displayed) GPI anchored CPG2(Q3) enzyme.

| Sequence Listing Free Text | |
|---|---|
| <210> | 1 |
| <223> | Description of Artificial Sequence: synthetic gene encoding CPG2 |
| <210> | 2 |
| <223> | Description of Artificial Sequence: synthetic CPG2 |
| <210> | 3 |
| <223> | Description of Artificial Sequence: synthetic oligonucleotide |
| <210> | 4 |
| <223> | Description of Artificial Sequence: synthetic oligonucleotide |
| <210> | 5 |
| <223> | Description of Artificial Sequence: synthetic CPG2 with human antibody secretory leader |
| <210> | 6 |
| <223> | Description of Artificial Sequence: synthetic CPG2 with human antibody secretory leader |
| <210> | 7 |
| <223> | Description of Artificial Sequence: synthetic oligonucleotide |

| Sequence Listing Free Text | |
|---|---|
| <210> | 8 |
| <223> | Description of Artificial Sequence: synthetic oligonucleotide |
| <210> | 9 |
| <223> | Description of Artificial Secuence: synthetic oligonucleotide |
| <210> | 10 |
| <223> | Description of Artificial Sequence: CPG2 mutant |
| <210> | 11 |
| <223> | Description of Artificial Sequence: CPG2 mutant |
| <210> | 13 |
| <223> | Description of Artificial Sequence: synthetic oligonucleotide |
| <210> | 14 |
| <223> | Description of Artificial Sequence: synthetic oligonucleotide |
| <210> | 15 |
| <223> | Description of Artificial sequence: synthetic oligonucleotide |
| <210> | 16 |
| <223> | Description of Artificial Sequence: synthetic oligonucleotide |
| <210> | 17 |
| <223> | Description of Artificial Sequence: CPG2 mutant with last exon of Thy-1 fused at 3' end |
| <210> | 18 |
| <223> | Description of Artificial Sequence: CPG2 vith last exon of Thy-1 fused at 3' end |

What is claimed is:

1. An expression vector expressing a glycosylphosphatidylinositol (GPI)-enzyme hybrid anchored to a surface of a mammalian cell comprising:

i) a polynucleotide sequence encoding a signal peptide;

ii) a polynucleotide sequence encoding an enzyme which activates a prodrug;

iii) a polynucleotide sequence encoding a post-translational GPI addition motif;

and wherein sequences i), ii) and iii) are functionally positioned in this order relative to each other in the 5' to 3' direction of the sense strand of the vector; the enzyme does not have a GPI addition motif where the enzyme occurs naturally; and whereby on expression of the vector in the mammalian cell, the enzyme is anchored to the surface of the cell via a GPI moiety post-translationally added to the enzyme by the mammalian cell whereby the GPI-enzyme hybrid is formed; and wherein the enzyme is carboxypeptidase G2 comprising unaltered glycosylation sites.

2. The expression vector according to claim 1 wherein the GPI addition motif comprises a C-terminal sequence of a protein selected from decay accelerating factor (DAF), human placental alkaline phosphatase (HPAP), lymphocyte function associated antigen-3 (LFA-3) and Thy-1.

3. The expression vector according to claim 1 wherein i) the post-translational GPI addition motif is SEQ ID NO: 12.

4. The expression vector of claim 1 in a pharmaceutically acceptable carrier.

5. A pharmaceutical pack comprising i) a first pharmaceutical composition comprising the expression vector of claim 1, and ii) a second pharmaceutical composition comprising a prodrug activated by the enzyme encoded by the expression vector in the first pharmaceutical composition and a pharmaceutically acceptable diluent or carrier.

6. The pharmaceutical pack according to claim 5 comprising an enzyme/prodrug combination in which the prodrug is selected from N-(4-[N,N-bis(2-iodoethyl)amino]phenoxycarbonyl)-L-glutamic acid, N-(4-[N,N-bis(2-chloroethyl)amino]-phenoxycarbonyl)-L-glutamic-gamma-(3,5-dicarboxy)anilide and or N-(4-[N,N-bis(2-chloroethyl)amino]-phenoxycarbonyl)-L-glutamic acid or a pharmaceutically acceptable salt of said prodrug.

* * * * *

```
                       SEQUENCE LISTING

<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 1
acataccagc tctgcaccag ctgtac                                      26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 2
acataccagc tctgcaccag ctgcgc                                      26

<210> SEQ ID NO 3
<211> LENGTH: 22
<212> TYPE: DNA
<213> ORGANISM: Artificial Sequence
```

```
<220> FEATURE:
<223> OTHER INFORMATION: Description of Artificial Sequence: Primer

<400> SEQUENCE: 3
cagggagaac ccaccccgg at                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
ggagcccaag aacacgtcca cg                                             22

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 5
cgcggcgtca cgtaagggcc gccgccgcgc agtccgtcct ctcaggtgca gatgtac       57

<210> SEQ ID NO 6
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 6
cgcggcgtca cgtaagggcc gccgccgcgc agtccgtcct ctcaggtgca gatgctt       57

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 7
cagtgacttc catagagaca gaa                                            23

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 8
cgcggcgaac ccaccccctg ctgccgcgcc tcaccatcct cctggcgc                 48

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 9
cgcggcgaac ccaccccctg ctgccgcgcc tcaccatcct cctggcgg                 48
```